US006790210B1

(12) United States Patent
Cragg et al.

(10) Patent No.: US 6,790,210 B1
(45) Date of Patent: Sep. 14, 2004

(54) METHODS AND APPARATUS FOR FORMING CURVED AXIAL BORES THROUGH SPINAL VERTEBRAE

(75) Inventors: Andrew H. Cragg, Edina, MN (US); Jonathan Kagan, Hopkins, MN (US)

(73) Assignee: TranS1, Inc., Wilmington, NC (US)

( * ) Notice: Subject to any disclaimer, the term of this patent is extended or adjusted under 35 U.S.C. 154(b) by 172 days.

(21) Appl. No.: 09/709,105

(22) Filed: Nov. 10, 2000

Related U.S. Application Data

(60) Provisional application No. 60/182,748, filed on Feb. 16, 2000.

(51) Int. Cl.[7] .............................................. A61B 17/16
(52) U.S. Cl. ............................ 606/80; 606/180; 606/61
(58) Field of Search ............................. 606/61, 79, 80, 606/85, 180

(56) References Cited

U.S. PATENT DOCUMENTS

| | | | |
|---|---|---|---|
| 1,630,239 A | 5/1927 | Binkley et al. | |
| 3,367,326 A | 2/1968 | Frazier | |
| 3,554,192 A | 1/1971 | Isberner | |
| 3,892,232 A | 7/1975 | Neufeld | 128/92 EB |
| 4,135,506 A | 1/1979 | Ulrich | |
| 4,170,990 A | 10/1979 | Baumgart et al. | 128/92 B |
| 4,265,231 A | 5/1981 | Scheller, Jr. et al. | 128/92 E |
| 4,401,112 A | 8/1983 | Rezaian | 128/92 B |
| 4,453,539 A | 6/1984 | Raftopoulos et al. | 128/92 BC |
| 4,541,423 A | 9/1985 | Barber | 128/92 E |
| 4,553,273 A | 11/1985 | Wu | 623/18 |
| 4,554,914 A | 11/1985 | Kapp et al. | |
| 4,573,448 A | 3/1986 | Kambin | |
| 4,636,217 A | 1/1987 | Ogilvie et al. | 623/17 |
| 4,756,649 A | 7/1988 | Heule | 408/178 |
| 4,844,088 A | 7/1989 | Kambin | |

(List continued on next page.)

FOREIGN PATENT DOCUMENTS

| | | |
|---|---|---|
| EP | 0 611 116 B1 | 4/1994 |
| EP | 0 980 677 A1 | 2/2000 |

(List continued on next page.)

OTHER PUBLICATIONS

Friedrich W. Rathke and Karl F. Schlegel—Surgery of the Spine—Atlas of Orthopaedic Operations, vol. 1—1979—pp 222–224.

(List continued on next page.)

*Primary Examiner*—D. Jacob Davis
(74) *Attorney, Agent, or Firm*—Knobbe, Martens, Olson & Bear, LLP.

(57) ABSTRACT

One or more curved axial bore is formed commencing from an anterior or posterior sacral target point and cephalad through vertebral bodies in general alignment with a visualized, trans-sacral axial instrumentation/fusion (TASIF) line in a minimally invasive, low trauma, manner. An anterior axial instrumentation/fusion line (AAIFL) or a posterior axial instrumentation/fusion line (PAIFL) that extends from the anterior or posterior target point, respectively, in the cephalad direction following the spinal curvature through one or more vertebral body is visualized by radiographic or fluoroscopic equipment. Generally curved anterior or posterior TASIF axial bores are formed in axial or parallel or diverging alignment with the visualized AAIFL or PAIFL, respectively. The anterior and posterior TASIF axial bore forming tools can be manipulated from proximal portions thereof to adjust the curvature of the anterior or posterior TASIF axial bores as they are formed in the cephalad direction. The boring angle of the distally disposed boring member or drill bit can be adjusted such that selected sections of the generally curved anterior or posterior TASIF axial bores can be made straight or relatively straight, and other sections thereof can be made curved to optimally traverse vertebral bodies and intervening disc, if present.

15 Claims, 18 Drawing Sheets

U.S. PATENT DOCUMENTS

| | | | |
|---|---|---|---|
| 4,862,891 A | 9/1989 | Smith | |
| RE33,258 E | 7/1990 | Onik et al. | |
| 4,966,604 A | 10/1990 | Reiss | |
| 4,969,888 A | 11/1990 | Scholten et al. | |
| 5,002,546 A | 3/1991 | Romano | 606/80 |
| 5,015,255 A | 5/1991 | Kuslich | 623/17 |
| 5,030,201 A | 7/1991 | Palestrant | 604/22 |
| 5,059,193 A | 10/1991 | Kuslich | 606/61 |
| 5,062,850 A | 11/1991 | MacMillan et al. | |
| 5,071,437 A | 12/1991 | Steffee, Arthur D. | |
| 5,171,279 A | 12/1992 | Mathews | |
| 5,190,546 A | 3/1993 | Jervis | 606/78 |
| 5,192,326 A | 3/1993 | Bao et al. | |
| 5,195,968 A | 3/1993 | Lundquist et al. | |
| 5,242,443 A | 9/1993 | Kambin | |
| 5,242,444 A | 9/1993 | MacMillan | |
| 5,242,461 A | 9/1993 | Kortenbach et al. | |
| 5,258,031 A | 11/1993 | Salib et al. | |
| 5,269,785 A | 12/1993 | Bonutti | |
| 5,285,795 A | 2/1994 | Ryan et al. | |
| 5,290,289 A | 3/1994 | Sanders et al. | 606/61 |
| 5,313,962 A | 5/1994 | Obenchain | |
| 5,336,223 A | 8/1994 | Rogers | 606/61 |
| 5,357,983 A | 10/1994 | Mathews | |
| 5,366,457 A | 11/1994 | McGuire et al. | |
| 5,383,884 A | 1/1995 | Summers | |
| 5,395,188 A | 3/1995 | Bailey et al. | 408/127 |
| 5,395,317 A | 3/1995 | Kambin | |
| 5,396,880 A | 3/1995 | Kagan et al. | 128/6 |
| 5,403,276 A | 4/1995 | Schechter et al. | |
| 5,415,661 A | 5/1995 | Holmes | 606/69 |
| 5,433,739 A | 7/1995 | Sluijter et al. | |
| 5,480,440 A | 1/1996 | Kambin | |
| 5,496,322 A | 3/1996 | Mathews | |
| 5,505,732 A | 4/1996 | Michelson | 606/61 |
| 5,514,137 A | 5/1996 | Coutts | 606/62 |
| 5,514,180 A | 5/1996 | Heggeness et al. | 623/17 |
| 5,545,228 A | 8/1996 | Kambin | |
| 5,549,679 A | 8/1996 | Kuslich | |
| 5,554,163 A | 9/1996 | Shturman | |
| 5,558,674 A | 9/1996 | Heggeness et al. | |
| 5,562,736 A | 10/1996 | Ray et al. | |
| 5,569,248 A | 10/1996 | Mathews | |
| 5,571,189 A | 11/1996 | Kuslich | 623/17 |
| 5,571,190 A | 11/1996 | Ulrich et al. | |
| 5,584,887 A | 12/1996 | Kambin | |
| 5,591,170 A | 1/1997 | Spievack et al. | |
| 5,630,816 A | 5/1997 | Kambin | |
| 5,653,708 A | 8/1997 | Howland | |
| 5,665,122 A | 9/1997 | Kambin | |
| 5,669,909 A | 9/1997 | Zdeblick et al. | |
| 5,700,291 A | 12/1997 | Kuslich et al. | 623/17 |
| 5,702,454 A | 12/1997 | Baumgartner | |
| 5,702,455 A | 12/1997 | Saggar | 623/17 |
| 5,713,904 A | 2/1998 | Errico et al. | 606/73 |
| 5,728,097 A | 3/1998 | Mathews | |
| 5,735,899 A | 4/1998 | Schwartz et al. | 623/17 |
| 5,741,253 A | 4/1998 | Michelson | |
| 5,741,261 A | 4/1998 | Moskovitz et al. | |
| 5,762,629 A | 6/1998 | Kambin | |
| 5,785,709 A | 7/1998 | Kummer et al. | |
| 5,792,044 A | 8/1998 | Foley et al. | |
| 5,827,328 A | 10/1998 | Buttermann | 623/17 |
| 5,885,292 A | 3/1999 | Moskovitz et al. | |
| 5,888,220 A | 3/1999 | Felt et al. | |
| 5,888,223 A | 3/1999 | Bray, Jr. | 623/17 |
| 5,891,147 A | 4/1999 | Moskovitz et al. | |
| 5,902,231 A | 5/1999 | Foley et al. | |
| 5,906,616 A | 5/1999 | Pavlov et al. | |
| 5,921,971 A | 7/1999 | Agro et al. | |
| 5,928,239 A | 7/1999 | Mirza | |
| 5,954,635 A | 9/1999 | Foley et al. | |
| 5,964,761 A | 10/1999 | Kambin | |
| 5,968,062 A | 10/1999 | Thomas et al. | |
| 5,972,015 A | 10/1999 | Scribner et al. | |
| 5,976,146 A | 11/1999 | Ogawa et al. | 606/86 |
| 5,976,187 A | 11/1999 | Richelsoph | 623/17 |
| 5,980,504 A | 11/1999 | Sharkey et al. | |
| 5,989,256 A | 11/1999 | Kuslich et al. | 606/74 |
| 6,007,487 A | 12/1999 | Foley et al. | |
| 6,010,495 A | 1/2000 | Tilton, Jr. | |
| 6,010,502 A | 1/2000 | Bagby | |
| 6,019,792 A | 2/2000 | Cauthen | |
| 6,022,362 A | 2/2000 | Lee et al. | |
| 6,030,162 A | 2/2000 | Huebner | |
| 6,033,406 A | 3/2000 | Mathews | |
| 6,036,696 A * | 3/2000 | Lambrecht et al. | 606/97 |
| 6,053,916 A | 4/2000 | Moore | |
| 6,056,749 A | 5/2000 | Kuslich | 606/61 |
| 6,066,152 A | 5/2000 | Strauss et al. | |
| 6,066,154 A | 5/2000 | Reiley et al. | |
| 6,080,099 A | 6/2000 | Slater et al. | |
| 6,086,589 A | 7/2000 | Kuslich et al. | 606/61 |
| 6,093,207 A | 7/2000 | Pisharodi | 623/17 |
| 6,095,149 A | 8/2000 | Sharkey et al. | |
| 6,120,502 A | 9/2000 | Michelson | |
| 6,123,705 A | 9/2000 | Michelson | |
| 6,127,597 A | 10/2000 | Beyar et al. | |
| 6,152,871 A | 11/2000 | Foley et al. | |
| 6,162,170 A | 12/2000 | Foley et al. | |
| 6,175,758 B1 | 1/2001 | Kambin | |
| 6,176,823 B1 | 1/2001 | Foley et al. | |
| 6,187,000 B1 | 2/2001 | Davison et al. | |
| 6,206,822 B1 | 3/2001 | Foley et al. | |
| 6,206,826 B1 | 3/2001 | Mathews et al. | |
| 6,210,412 B1 | 4/2001 | Michelson | |
| 6,217,509 B1 | 4/2001 | Foley et al. | |
| 6,241,734 B1 | 6/2001 | Scribner et al. | |
| 6,264,656 B1 | 7/2001 | Michelson | |
| 6,287,313 B1 | 9/2001 | Sasso | |
| 6,315,795 B1 | 11/2001 | Scarborough et al. | |
| 6,371,990 B1 | 4/2002 | Ferree | |
| 6,379,334 B1 | 4/2002 | Frassica | |
| 6,383,188 B2 | 5/2002 | Kuslich et al. | |
| 6,383,190 B1 | 5/2002 | Preissman | |
| 6,387,130 B1 | 5/2002 | Stone et al. | |
| 6,395,007 B1 | 5/2002 | Bhatnagar et al. | |
| 6,402,750 B1 | 6/2002 | Atkinson et al. | |
| 6,409,766 B1 | 6/2002 | Brett | |
| 6,416,515 B1 | 7/2002 | Wagner | |
| 6,419,678 B1 | 7/2002 | Asfora | |
| 6,423,095 B1 | 7/2002 | Van Hoeck et al. | |
| 6,436,098 B1 | 8/2002 | Michelson | |
| 6,436,140 B1 | 8/2002 | Liu et al. | |
| 6,436,143 B1 | 8/2002 | Ross et al. | |
| 6,440,138 B1 | 8/2002 | Reiley et al. | |
| 6,447,514 B1 | 9/2002 | Stalcup et al. | |
| 6,447,518 B1 | 9/2002 | Krause et al. | |
| 6,447,546 B1 | 9/2002 | Bramlet et al. | |
| 6,447,547 B1 | 9/2002 | Michelson | |
| 6,540,747 B1 | 4/2003 | Marino | |
| 6,562,046 B2 | 5/2003 | Sasso | |
| 2002/0022888 A1 | 2/2002 | Serhan et al. | |
| 2002/0032444 A1 | 3/2002 | Mische | |
| 2002/0038123 A1 | 3/2002 | Visotsky et al. | |
| 2002/0072801 A1 | 6/2002 | Michelson | |
| 2002/0077632 A1 | 6/2002 | Tsou | |
| 2002/0077700 A1 | 6/2002 | Varga et al. | |
| 2002/0077702 A1 | 6/2002 | Castro | |
| 2002/0107573 A1 | 8/2002 | Steinberg | |
| 2002/0147485 A1 | 10/2002 | Mamo et al. | |

FOREIGN PATENT DOCUMENTS

| WO | WO 95/22285 | 8/1995 |
|----|----|----|
| WO | WO 97/40878 | 11/1997 |
| WO | WO 98/38918 | 9/1998 |
| WO | WO 00/67650 | 11/2000 |
| WO | WO 01/28468 A1 | 4/2001 |
| WO | WO 01/60268 A1 | 8/2001 |
| WO | WO 02/09801 A1 | 2/2002 |
| WO | WO 02/13732 A2 | 2/2002 |
| WO | WO 02/34120 A2 | 5/2002 |
| WO | WO 02/058599 A2 | 8/2002 |

OTHER PUBLICATIONS

J. J. Trambert, MD, "Percutaneous Interventions in the Presacral Space: CT–guided Precoccygeal Approach—Early Experience", *Radiology 1999*; 213:901–904.

R. Johnsson et al., "Posterolateral lumbar fusion using facet joint fixation with biodegradable rods: a pilot study", *Eur Spine J.*, (1997) 6:144–148.

R. P. Louis, MD, "Anatomy, Physiology, and Biomechanics of the Lumbopelvic Junction", *Lumbosacral and Spinopelvic Fusion*, Chapter 1 (pp. 1–11) Lippincott–Raven Pub. (1996).

M. R. Zindrick, MD et al., "Clinical Anatomy of the Lumbrosacral Junction and Pelvis" *Lumbosacral and Spinopelvic Fusion*, Chapt. 2 (pp. 13–25) Lippincott–Raven Pub. (1996).

J. W. Olgilvie, MD et al., "Overview of Fixation to the Sacrum & Pelvis in Spinal Surgery", *Lumbosacral and Spinopelvic Fusion*, Chapter 17 (pp. 191–198) Lippincott–Raven Pub. (1996).

S. A. Caruso, ME et al., "Instrumented Fusions of the Lumbosacral Spine: A Technical Overview", *Lumbosacral and Spinopelvic Fusion*, Chapter 18 (pp. 199–210) Lippincott–Raven Pub. (1996).

R. P. Louis, MD, "Lumbopelvic Fusion", *Lumbosacral and Spinopelvic Fusion*, Chapter 38 (pp. 479–492) Lippincott–Raven Pub. (1996).

J. Dove, FRCS, "The Hartshill System for the Front of the Lumbosacral Spine", *Lumbosacral and Spinopelvic Fusion*, Chapter 42 (pp. 539–543) Lippincott–Raven Pub. (1996).

P. Kambin, MD et al., "Arthroscopic Fusion of the Lumbosacral Spine", *Lumbosacral and Spinopelvic Fusion*, Chapter 44 (pp. 565–577) Lippincott–Raven Pub. (1996).

Jason A. Smith, MD, et al., Clinical Outcome of Trans–Sacral Interbody Fusion After Partial Reduction for High–Grade L5–S1 Spondylolisthesis *Spine*, 2001, vol. 26, No. 20, pp. 2227–2234.

Michael MacMilland, MD, et al., "Percutaneous Lumbosacral Fixation and Fusion," *Percutaneous Spine Techniques*, Jan. 1996, vol. 7, No. 1, pp. 99–106.

Curtis A. Dickman, M.D., et al., "Transpedicular screw–rod fixation of the lumbar spine: operative technique and outcome in 104 cases," *J. Neurosurg*, Dec., 1992, vol. 77,pp. 860–870.

Richard M. Slone, MD, et al., "Spinal Fixation, Part 1, Basic Hardware, and Fixation Techniques for the Cervical Spine," *RadioGraphics*, 1993, vol. 13, No. 2, pp. 341–356.

Richard M. Slone, MD, et al., "Spinal Fixation, Part 2, Fixation Techniques and Hardware for the Thoracic and Lumbosacral Spine," *RadioGraphics*, 1993, vol. 13, No. 3, pp. 521–543.

Michael MacMillan, et al., "Biomechanical Analysis of a New Anterior Spine Implant for Post–Corpectomy Instability," *Journal of Spinal Disorders*, 1995, vol. 8, No. 1, pp. 56–61.

Hallett H. Mathews, M.D., "Minimally Invasive Fusion Techniques, Percutaneous Interbody Fusions," *Orthopedic Clinics of North America*, Oct. 1998, vol. 29, No. 4.

Parviz Kambin, M.D., et al., "Arthroscopic Microdiscectomy: An Alternative to Open Disc Surgery," *The Mount Sinai Journal of Medicine*, Sep. 2000, vol. 67, No. 4.

Hallett H. Mathews, M.D., et al., "Perspectives on Modern Orthopaedics, Minimally Invasive Techniques for theTreatment of Intervertebral Disk Herniation," *Journal of the American Academy of Orthopaedic Surgeons*, Mar./Apr. 2002, vol. 10, No. 2.

Parviz Kambin, M.D., "Percutaneous Spine Techniques, Diagnostic and Therapeutic Spinal Arthroscopy," *Neurosurgery Clinics of North America*, Jan. 1996, vol. 7, No. 1.

Parviz Kambin, M.D., et al., "Arthroscopic Discectomy of the Lumbar Spine," *Clinical Orthopaedics and Related Research*, Apr. 1997, No. 337.

U.S. patent application Publication No. 2002/0082598 A1, *Percutaneous Vertebral Fusion System*, published Jun. 27, 2002.

U.S. patent application Publication No. 2002/0068939 A1, *Expandable Orthopedic Device*, published Jun. 6, 2002.

John L. Emmett, M.D., M.S. (Urology), David M. Witten, M.D., M.S. (Radiology)—vol. 1, Third Edition—Clinical Urography—An Atlas and Textbook of Roentgenologic Diagnosis—1971—Phneumography (Retroperitoneal Gas [Air] Insufflation; Perirenal Insufflation; Presacral Insufflation).

* cited by examiner

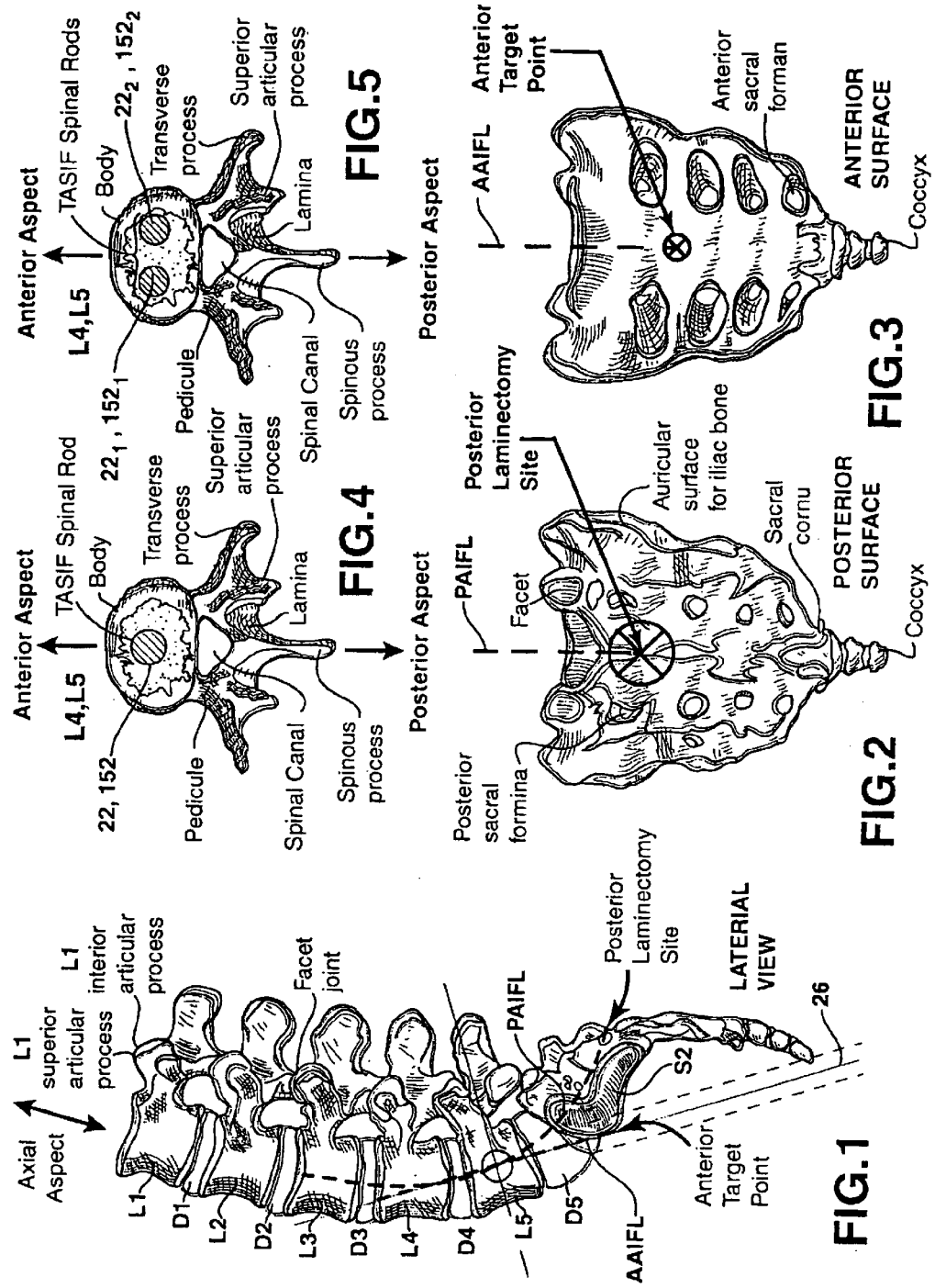

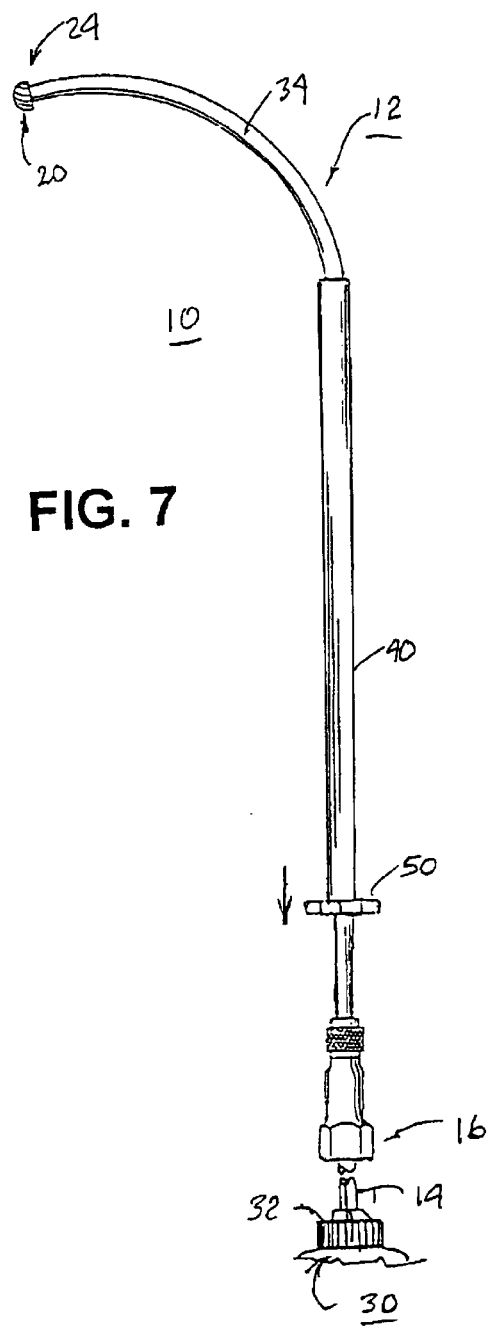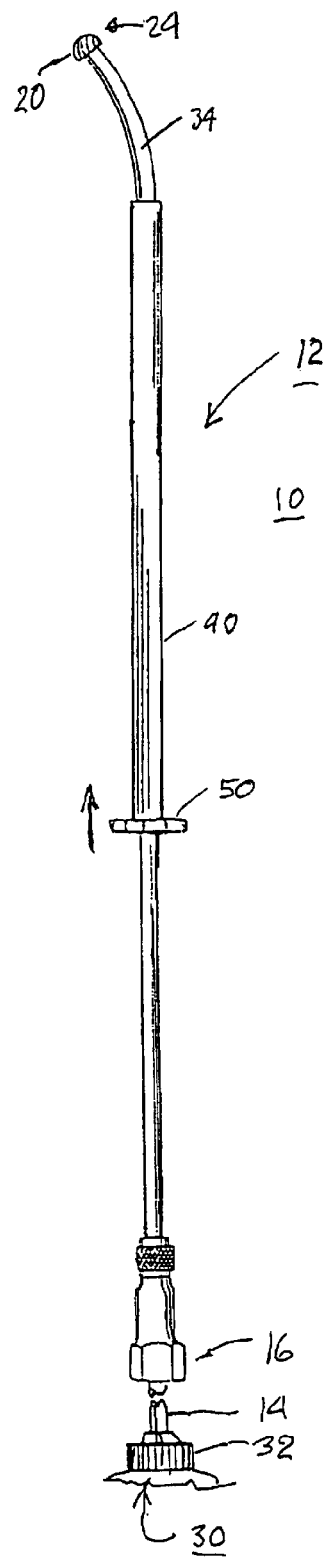
FIG. 7
FIG. 8

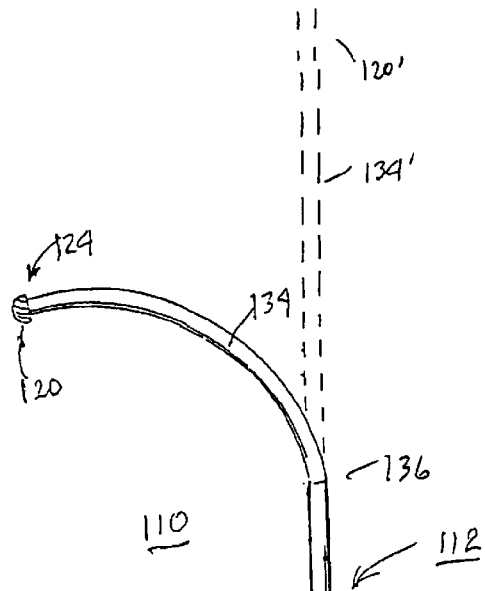
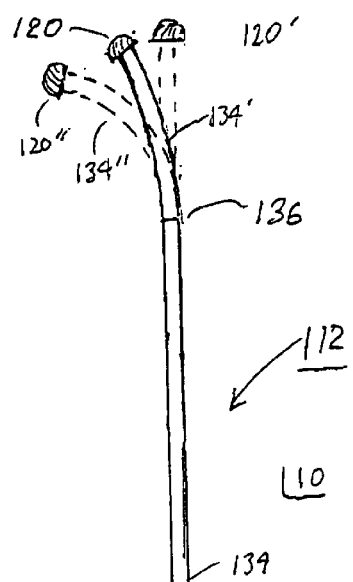
FIG. 19
FIG. 20
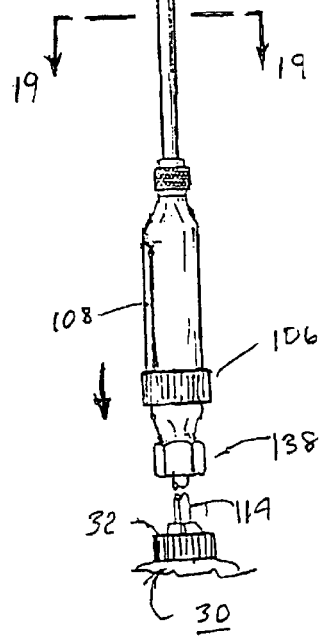
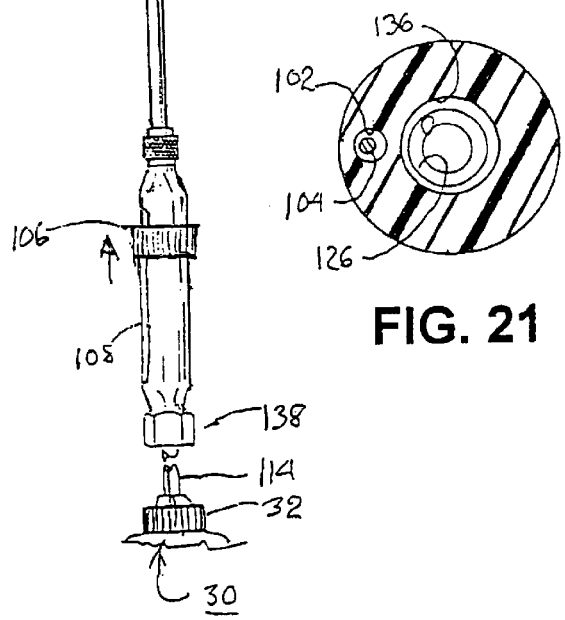
FIG. 21

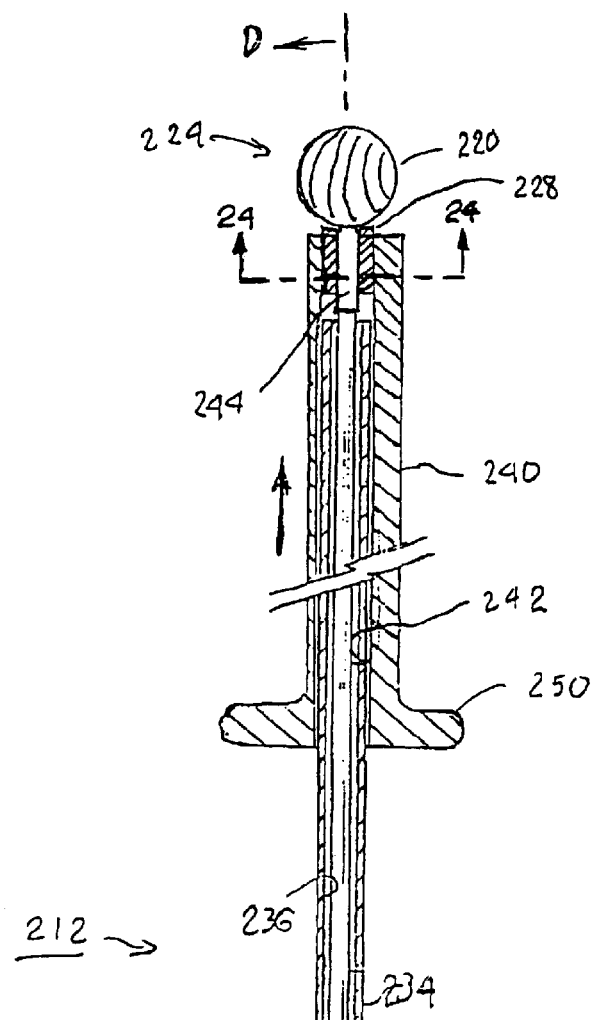
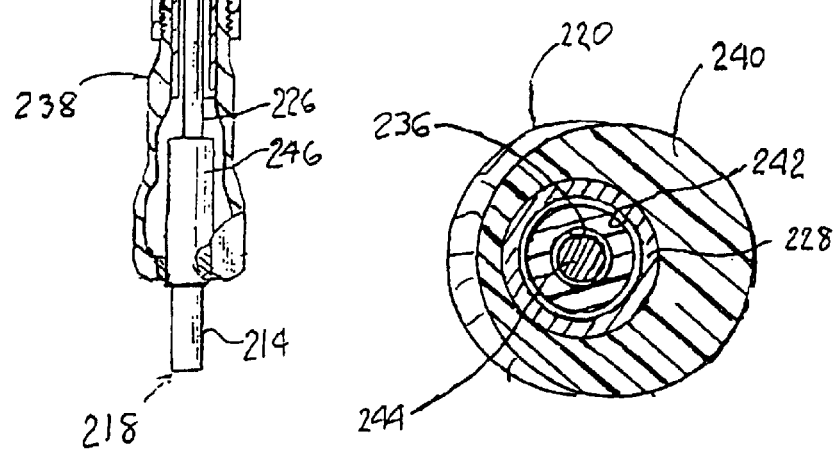
FIG. 23
FIG. 24

METHODS AND APPARATUS FOR FORMING CURVED AXIAL BORES THROUGH SPINAL VERTEBRAE

This application claims priority and benefits from Provisional Patent application No. 60/182,748, filed Feb. 16, 2000 entitled METHOD AND APPARATUS FOR TRANS-SACRAL SPINAL FUSION.

CROSS-REFERENCE TO RELATED APPLICATIONS

Reference is hereby made to commonly assigned co-pending U.S. patent application Ser. No. (1) 09/640,222 filed Aug. 16,2000, for METHOD AND APPARATUS FOR PROVIDING POSTERIOR OR ANTERIOR TRANS-SACRAL ACCESS TO SPINAL VERTEBRAE in the name of Andrew H. Cragg, MD; (2) Ser. No. 09/684,620 filed Oct. 10, 2000, for AXIAL SPINAL IMPLANT AND METHOD AND APPARATUS FOR IMPLANTING AN AXIAL SPINAL IMPLANT WITHIN THE VERTEBRAE OF THE SPINE in the name of Andrew H. Cragg, MD; and (3) Ser. No. 09/710,369 filed on even date herewith for METHODS AND APPARATUS FOR FORMING SHAPED AXIAL BORES THROUGH SPINAL VERTEBRAE in the name of Andrew H. Cragg, MD et al.

FIELD OF THE INVENTION

The present invention relates generally to spinal surgery, particularly methods and apparatus for forming one or more curved axial bore through vertebral bodies in general alignment with a visualized, trans-sacral axial instrumentation/fusion (TASIF) line in a minimally invasive, low trauma, manner.

BACKGROUND OF THE INVENTION

It has been estimated that 70% of adults have had a significant episode of back pain or chronic back pain emanating from a region of the spinal column or backbone. Many people suffering chronic back pain or an injury requiring immediate intervention resort to surgical intervention to alleviate their pain.

The spinal column or back bone encloses the spinal cord and consists of 33 vertebrae superimposed upon one another in a series which provides a flexible supporting column for the trunk and head. The vertebrae cephalad (i.e., toward the head or superior) to the sacral vertebrae are separated by fibrocartilaginous intervertebral discs and are united by articular capsules and by ligaments. The uppermost seven vertebrae are referred to as the cervical vertebrae, and the next lower twelve vertebrae are referred to as the thoracic, or dorsal, vertebrae. The next lower succeeding five vertebrae below the thoracic vertebrae are referred to as the lumbar vertebrae and are designated L1–L5 in descending order. The next lower succeeding five vertebrae below the lumbar vertebrae are referred to as the sacral vertebrae and are numbered S1–S5 in descending order. The final four vertebrae below the sacral vertebrae are referred to as the coccygeal vertebrae. In adults, the five sacral vertebrae fuse to form a single bone referred to as the sacrum, and the four rudimentary coccyx vertebrae fuse to form another bone called the coccyx or commonly the "tail bone". The number of vertebrae is sometimes increased by an additional vertebra in one region, and sometimes one may be absent in another region.

Typical lumbar, thoracic and cervical vertebrae consist of a ventral or vertebral body and a dorsal or neural arch. In the thoracic region, the ventral body bears two costal pits for reception of the head of a rib on each side. The arch which encloses the vertebral foramen is formed of two pedicles and two lamina. A pedicle is the bony process which projects backward or anteriorly from the body of a vertebra connecting with the lamina on each side. The pedicle forms the root of the vertebral arch. The vertebral arch bears seven processes: a dorsal spinous process, two lateral transverse processes, and four articular processes (two superior and two inferior). A deep concavity, inferior vertebral notch, on the inferior border of the arch provides a passageway or spinal canal for the delicate spinal cord and nerves. The successive vertebral foramina surround the spinal cord. Articulating processes of the vertebrae extend posteriorly of the spinal canal.

The bodies of successive lumbar, thoracic and cervical vertebrae articulate with one another and are separated by intervertebral discs formed of fibrous cartilage enclosing a central mass, the nucleus pulposus that provides for cushioning and dampening of compressive forces to the spinal column. The intervertebral discs are anterior to the vertebral canal. The inferior articular processes articulate with the superior articular processes of the next succeeding vertebra in the caudal (i.e., toward the feet or inferior) direction. Several ligaments (supraspinous, interspinous, anterior and posterior longitudinal, and the ligamenta flava) hold the vertebrae in position yet permit a limited degree of movement.

The relatively large vertebral bodies located in the anterior portion of the spine and the intervertebral discs provide the majority of the weight bearing support of the vertebral column. Each vertebral body has relatively strong bone comprising the outside surface of the body and weak bone comprising the center of the vertebral body.

Various types of spinal column disorders are known and include scoliosis (abnormal lateral curvature of the spine), kyphosis (abnormal forward curvature of the spine, usually in the thoracic spine), excess lordosis (abnormal backward curvature of the spine, usually in the lumbar spine), spondylolisthesis (forward displacement of one vertebra over another, usually in the lumbar or cervical spine) and other disorders, such as ruptured or slipped discs, degenerative disc disease, fractured vertebra, and the like. Patients who suffer from such conditions usually experience extreme and debilitating pain and often neurologic deficit in nerve function.

Approximately 95% of spinal surgery involves the lower lumbar vertebrae designated as the fourth lumbar vertebra ("L4"), the fifth lumbar vertebra ("L5"), and the first sacral vertebra ("S1"). Persistent low back pain is attributed primarily to degeneration of the disc connecting L5 and S1. Surgical procedures have been developed and used to remove the disc and fuse the vertebral bodies together and/or to stabilize the intervertebral structures. Although damaged discs and vertebral bodies can be identified with sophisticated diagnostic imaging, the surgical procedures are so extensive that clinical outcomes are not consistently satisfactory. Furthermore, patients undergoing presently available fusion surgery experience significant complications and uncomfortable, prolonged convalescence.

A number of devices and techniques involving implantation of spinal implants to reinforce or replace removed discs and/or anterior portions of vertebral bodies and which mechanically immobilize areas of the spine assisting in the eventual fusion of the treated adjacent vertebrae have also been employed or proposed over the years In order to overcome the disadvantages of purely surgical techniques. Such techniques have been used effectively to treat the above described conditions and to relieve pain suffered by the patient However, there are still disadvantages to the present fixation implants and surgical implantation techniques. The historical development of such implants is set forth in U.S. Pat. Nos. 5,505,732, 5,514,180, and 5,888,223, for example.

One technique for spinal fixation includes the immobilization of the spine by the use of spine rods of many different configurations that run generally parallel to the spine. Typically, the posterior surface of the spine is isolated and bone screws are first fastened to the pedicles of the appropriate vertebrae or to the sacrum and act as anchor points for the spine rods. The bone screws are generally placed two per vertebra, one at each pedicle on either side of the spinous process. Clamp assemblies join the spine rods to the screws. The spine rods are generally bent to achieve the desired curvature of the spinal column. Wires may also be employed to stabilize rods to vertebrae. These techniques are described further in U.S. Pat. No. 5,415,661, for example.

These types of rod systems can be effective, but require a posterior approach and implanting screws into or clamps to each vertebra over the area to be treated. To stabilize the implanted system sufficiently, one vertebra above and one vertebra below the area to be treated are often used for implanting pedicle screws. Since the pedicles of vertebrae above the second lumbar vertebra (L2) are very small, only small bone screws can be used which sometimes do not give the needed support to stabilize the spine. These rods and screws and clamps or wires are surgically fixed to the spine from a posterior approach, and the procedure is difficult. A large bending moment is applied to such rod assemblies, and because the rods are located outside the spinal column, they depend on the holding power of the associated components which can pull out of or away from the vertebral bone.

In a variation of this technique disclosed in U.S. Pat. Nos. 4,553,273 and 4,636,217, both described in U.S. Pat. No. 5,735,899, two of three vertebrae are joined by surgically obtaining access to the interior of the upper and lower vertebral bodies through excision of the middle vertebral body. In the '899 patent, these approaches are referred to as "intraosseous" approaches, although they are more properly referred to as "interosseous" approaches by virtue of the removal of the middle vertebral body. The removal is necessary to enable a lateral insertion of the implant into the space it occupied so that the opposite ends of the implant can be driven upward and downward into the upper and lower vertebral bodies. These approaches are criticized as failing to provide adequate medial-lateral and rotational support in the '899 patent. In the '899 patent, an anterior approach is made, slots are created in the upper and lower vertebrae, and rod ends are fitted into the slots and attached to the remaining vertebral bodies of the upper and lower vertebrae by laterally extending screws.

A number of disc shaped replacements or artificial disc implants and methods of insertion have been proposed as disclosed, for example, in U.S. Pat. Nos. 5,514,180 and 5,888,223, for example. A further type of disc reinforcement or augmentation implant that has been clinically employed for spinal fusion comprises a hollow cylindrical titanium cage that is externally threaded and is screwed laterally into place in a bore formed in the disc between two adjacent vertebrae. Bone grafts from cadavers or the pelvis or substances that promote bone growth are then packed into the hollow center of the cage to encourage bone growth (or ingrowth) through the cage pores to achieve fusion of the two adjacent vertebrae. Two such cage implants and the surgical tools employed to place them are disclosed in U.S. Pat. Nos. 5,505,732 and 5,700,291, for example. The cage implants and the associated surgical tools and approaches require precise drilling of a relatively large hole for each such cage laterally between two adjacent vertebral bodies and then threading a cage into each prepared hole. The large hole or holes can compromise the integrity of the vertebral bodies, and if drilled too posteriorly, can injure the spinal cord. The end plates of the vertebral bodies, which comprise very hard bone and help to give the vertebral bodies needed strength, are usually destroyed during the drilling. The cylindrical cage or cages are now harder than the remaining bone of the vertebral bodies, and the vertebral bodies tend to collapse or "telescope," together. The telescoping causes the length of the vertebral column to shorten and can cause damage to the spinal cord and nerves that pass between the two adjacent vertebrae.

Methods and apparatus for accessing the discs and vertebrae by lateral surgical approaches are described in U.S. Pat. No. 5,976,146. The intervening muscle groups or other tissues are spread apart by a cavity forming and securing tool set disclosed in the '146 patent to enable endoscope aided, lateral access to damaged vertebrae and discs and to perform corrective surgical procedures.

A compilation of the above described surgical techniques and spinal implants and others that have been used clinically is set forth in certain chapters of the book entitled *Lumbosacral and Spinopelvic Fixation*, edited by Joseph Y. Margolies et al. (Lippincott-Raven Publishers, Philadelphia, 1996). Attention is directed particularly to Chapters 1, 2, 17, 18, 38, 42 and 44. In "Lumbopelvic Fusion" (Chapter 38, by Prof. Rene P. Louis, MD) techniques for repairing a spondylolisthesis, in this case, a severe displacement of L5 with respect to S1 and the intervening disc, are described and depicted. An anterior lateral exposure of L5 and S1 is made, a discectomy is performed, and the orientation of L5 to S1 is mechanically corrected using a reduction tool, if the displacement is severe. A fibula graft or metal Judet screw is inserted as a dowel through a bore formed extending caudally through L5 and into S1. When the screw is used, bone growth material, e.g., bone harvested from the patient, is inserted into the bore alongside the screw, and the disc space is filled with bone sutured to the screw to keep it in place between the vertebral surfaces to act as a spacer implant occupying the extracted disc between L5 and S1. External bridge plates or rods are also optionally installed. The posterolateral or anterior lateral approach is necessitated to correct the severe spondylolisthesis displacement using the reduction tool and results in tissue injury. Because of this approach and need, the caudal bore and inserted the Judet screw can only traverse L5 and S1.

A similar anterior approach for treating spondylolisthesis is disclosed in U.S. Pat. No. 6,056,749. In this approach, a bore hole is formed in a cephalad vertebral body and extends through the intervening disc into a caudal vertebral body, the disc is removed, a disk cage is inserted laterally into the disc space, and an elongated, hollow threaded shaft is inserted into the bore and through a hole in the disc cage. The disk cage takes the place of the harvested bone disc inserts and its interlocking intersection with the shaft takes the place of the sutures employed to tie the harvested bone disc inserts to the screw in the technique described in the above-referenced Chapter 38 publication.

The above-described spinal implant approaches involve highly invasive surgery that laterally exposes the anterior or posterior portions of the vertebrae to be supported or fused.

Extensive muscular stripping and bone preparation can be necessary. As a result, the spinal column can be further weakened and/or result in surgery induced pain syndromes. Thus, presently used or proposed surgical fixation and fusion techniques involving the lower lumbar vertebrae suffer from numerous disadvantages. It is preferable to avoid the lateral exposure to correct less severe spondylolisthesis and other spinal injuries or defects affecting the lumbar and sacral vertebrae and discs.

A less intrusive posterior approach for treating spondylolisthesis is disclosed in U.S. Pat. No. 6,086,589, wherein a straight bore is formed through the sacrum from the exposed posterior sacral surface and in a slightly cephalad direction into the L5 vertebral body, preferably after realigning the vertebrae. A straight, hollow, threaded shaft with side wall holes restricted to the end portions thereof and bone growth material are inserted into the bore. A discectomy of the disc between L5 and S1 is preferably performed and bone ingrowth material is also preferably inserted into the space between the cephalad and caudal vertebral bodies. Only a limited access to and alignment of S1 and L5 can be achieved by this approach because the distal ends of the straight bore and shaft approach and threaten to perforate the anterior surface of the L5 vertebral body.

A wide variety of orthopedic implants have also been proposed or clinically employed to stabilize broken bones or secure artificial hip, knee and finger joints. Frequently, rods or joint supports are placed longitudinally within longitudinal bores made in elongated bones, e.g., the femur. A surgical method is disclosed in U.S. Pat. No. 5,514,137 for stabilizing a broken femur or other long bones using an elongated rod and resorbable cement. To accomplish a placement of a rod into any single bone, an end of a bone is exposed and a channel is drilled from the exposed end to the other end. Thereafter, a hollow rod is inserted, and resorbable cement is injected through the hollow rod, so as to provide fixation between the distal end of the rod and the cancellous tissue that surrounds the rod. A cement introducer device can also be used for the injection of cement. A brief reference is made in the '137 patent to the possibility of placing rods in or adjacent to the spine in the same manner, but no particular approach or devices are described.

Drilling tools are employed in many of the above described surgical procedures to bore straight holes into the vertebral bones. The boring of curved bores in other bones is described in U.S. Pat. Nos. 4,265,231, 4,541,423, and 5,002,546, for example. The '231 patent describes an elongated drill drive shaft enclosed within a pre-curved outer sheath that is employed to drill curved suture holding open ended bores into bones so that the suture passes through both open ends of the bore. The '423 patent describes an elongated flexible drill drive shaft enclosed within a malleable outer sheath that can be manually shaped into a curve before the bore is formed. The '546 patent describes a complex curve drilling tool employing a pivotal rocker arm and curved guide for a drill bit for drilling a fixed curve path through bone. All of these approaches dictate that the curved bore that is formed follow the predetermined and fixed curvature of the outer sheath or guide. The sheath or guide is advanced through the bore as the bore is made, making it not possible for the user to adjust the curvature of the bore to track physiologic features of the bone that it traverses.

SUMMARY OF THE INVENTION embodiments of the invention involve methods and apparatus for forming one or more axially extending curved bore through spinal vertebral bodies for performing surgical procedures, for receiving spinal implants or for other medical reasons wherein the curvature of sections of the curved bore can be adjusted by the surgeon to track the curvature of the spine.

The preferred embodiments of the present invention involve methods and apparatus including surgical tool sets for forming anterior and posterior TASIF axial bores extending from a respective anterior or posterior target point or position of an anterior or posterior sacral surface through at least one sacral vertebral body and one or more lumbar vertebral body in the cephalad direction. The anterior target point on the anterior sacral surface is accessed using a percutaneous tract extending from a skin incision through presacral space. The posterior target point on the posterior sacral surface is accessed using a surgical exposure of the posterior sacral surface. An anterior axial instrumentation/fusion line (AAIFL) or a posterior axial instrumentation/fusion line (PAIFL) that extends from the anterior or posterior target point, respectively, in the cephalad direction following the spinal curvature through one or more vertebral body is visualized by radiographic or fluoroscopic equipment. Generally curved anterior or posterior TASIF axial bores are formed in axial or parallel or diverging alignment with the visualized AAIFL or PAIFL, respectively.

The anterior and posterior TASIF axial bore forming tools of the present invention can be manipulated from proximal portions thereof that are located outside the patient's body to adjust the curvature of the anterior or posterior TASIF axial bores as they are formed in the cephalad direction. The boring angle of the distally disposed boring member or drill bit can be adjusted such that selected sections of the generally curved anterior or posterior TASIF axial bores can be made straight or relatively straight, and other sections thereof can be made curved to optimally traverse vertebral bodies and intervening discs, if present.

When a single anterior or posterior TASIF axial bore is formed, it can be formed in axial or parallel alignment with the visualized axial AAIFL and PAIFL. Similarly, multiple anterior or posterior TASIF axial bores can be formed all in parallel alignment with the visualized axial AAIFL and PAIFL or with at least one such TASIF axial bore formed in axial alignment with the visualized axial AAIFL and PAIFL.

Moreover, multiple anterior or posterior TASIF axial bores can be formed all commencing at the anterior or posterior target point and extending in the cephalad direction with each TASIF axial bore diverging apart from the other and away from the visualized axial AAIFL and PAIFL. The diverging TASIF axial bores terminate as spaced apart locations in a cephalad vertebral body or in separate cephalad vertebral bodies.

In certain embodiments, small diameter anterior and posterior TASIF axial bore forming tools can be employed in the same manner to form pilot holes extending in the cephalad direction through one or more sacral and lumbar vertebral bodies in alignment with the visualized AAIFL and PAIFL. The pilot holes can be used as part of anterior and posterior percutaneous tracts that are subsequently enlarged to form the anterior and posterior TASIF axial bores.

This summary of the invention and the objects, advantages and features thereof have been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein:

FIGS. 1–3 are lateral, posterior and anterior views of the lumbar and sacral portion of the spinal column depicting the visualized PAIFL and AAIFL extending cephalad and axially from the posterior laminectomy site and the anterior target point, respectively;

FIG. 4 is a sagittal caudal view of lumbar vertebrae depicting a TASIF spinal implant or rod within a TASIF axial bore formed following the visualized PAIFL or AAIFL of FIGS. 1–3;

FIG. 5 is a sagittal caudal view of lumbar vertebrae depicting a plurality, e.g., 2, TASIF spinal implants or rods within a like plurality of TASIF axial bores formed in parallel with the visualized PAIFL or AAIFL of FIGS. 1–3;

FIG. 7 is a plan view of one exemplary boring tool embodiment comprising an elongated drill shaft assembly and drill motor for forming a curved anterior or posterior TASIF axial bore, the drill bit having a 90° curve formed in the elongated drill drive shaft by retraction of an outer sheath;

FIG. 8 is a plan view of the boring tool of FIG. 7 with a reduced curvature formed in the elongated drill shaft assembly by adjustment of the outer sheath;

FIGS. 19–21 illustrate a further exemplary boring tool embodiment comprising an elongated drill shaft assembly and drill motor for forming a curved anterior or posterior TASIF axial bore in the manner illustrated in FIGS. 10–18;

FIGS. 22–25 illustrate a still further exemplary boring tool embodiment comprising an elongated drill shaft assembly and drill motor for forming a curved anterior or posterior TASIF axial bore in the manner illustrated in FIGS. 10–18;

DETAILED DESCRIPTION OF THE PREFERRED EMBODIMENTS OF THE INVENTION

Figure 6:
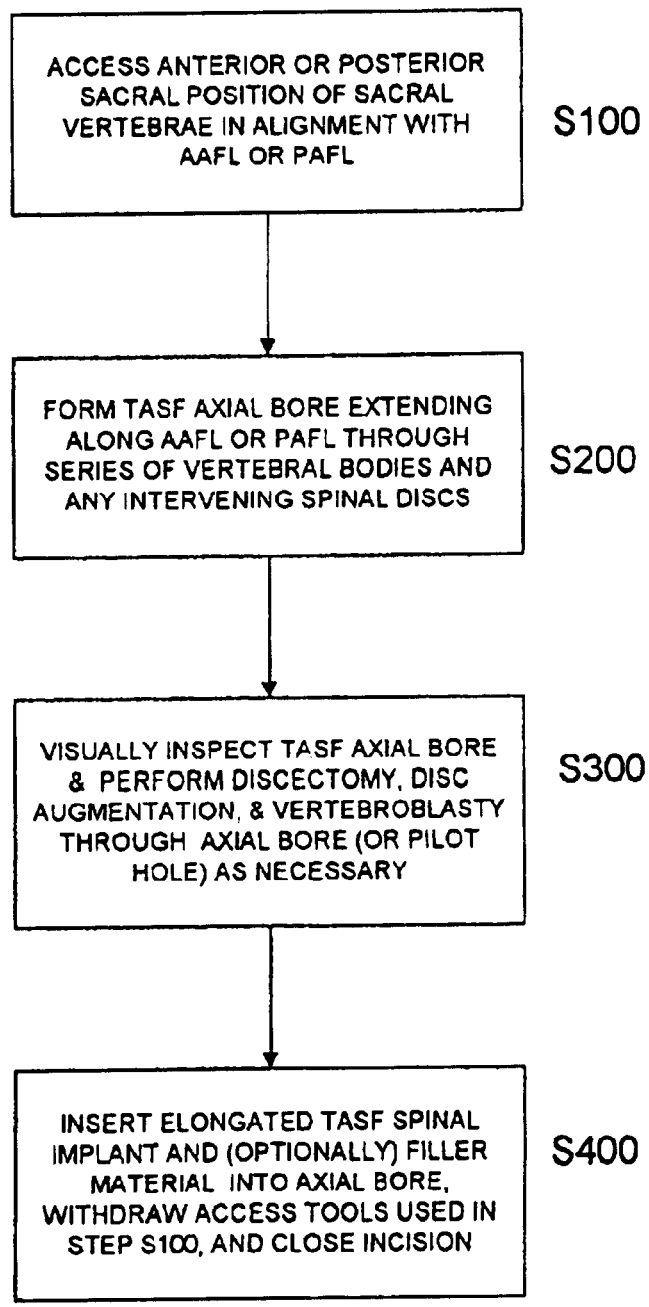
FIG. 6 is a simplified flow chart showing the principal surgical preparation steps of percutaneously accessing a posterior or anterior target point of the sacrum and forming a percutaneous tract following the visualized PAIFL or AAIFL of FIGS. 1–3, as well as subsequent steps of forming the TASIF bore(s) for treatment of accessed vertebral bodies and intervening discs and of implanting spinal implants therein.

The methods and surgical instrumentation and spinal implants disclosed in the above-referenced provisional application No. 60/182,748 and in co-pending, commonly assigned, patent application Ser. No. 09/640,222 filed Aug. 16,2000, for METHOD AND APPARATUS FOR PROVIDING POSTERIOR OR ANTERIOR TRANS-SACRAL ACCESS TO SPINAL VERTEBRAE can be employed in the practice of the present invention. The '222 application discloses a number of related TASIF methods and surgical tool sets for providing posterior and anterior trans-sacral access to a series of adjacent vertebrae located Within a human lumbar and sacral spine having an anterior aspect, a posterior aspect and an axial aspect, the vertebrae separated by intact or damaged spinal discs. Certain of the tools are selectively employed to form a percutaneous (i.e., through the skin) pathway from an anterior or posterior skin incision to a respective anterior or posterior position, e.g., a target point of a sacral surface or the cephalad end of a pilot hole bored through the sacrum and one or more lumbar vertebrae. The percutaneous pathway is generally axially aligned with the AAIFL or the PAIFL extending from the respective anterior or posterior target point through at least one sacral vertebral body and one or more lumbar vertebral body in the cephalad direction as visualized by radiographic or fluoroscopic equipment. The AAIFL and PAIFL follow the curvature of the vertebral bodies that they extend through in the cephalad direction.

Attention is first directed to the following description of FIGS. 1–6 is taken from the above-referenced parent provisional application No. 60/182,748. The acronyms TASF, AAFL, and PAFL used in the '748 application are changed to TASIF, AAIFL and PAIFL in this application to explicitly acknowledge that instruments can be introduced for inspection or treatments in addition to the fusion and fixation provided by spinal implants that may be inserted into the axial bores or pilot holes.

FIGS. 1–3 schematically illustrate the anterior and posterior TASIF surgical approaches in relation to the lumbar region of the spinal column, and FIGS. 4–5 illustrate the location of the TASIF implant or pair of TASIF implants within a corresponding posterior TASIF axial bore 22 or anterior TASIF axial bore 152 or pair of TASIF axial bores $22_1$, $22_2$ or $152_1$, $152_2$. Two TASIF axial bores and spinal implants or rods are shown in FIG. 5 to illustrate that a plurality, that is two or more, of the same may be formed and/or employed in side by side relation parallel with the AAIFL or PAIFL. Preferred TASIF surgical approaches for providing anterior and posterior trans-sacral access depicted in FIGS. 1–3 and preparing the TASIF axial bores 22 or 152 or $22_1$, $22_2$, or $152_1$, $152_2$ shown in FIGS. 4 and 5 are illustrated in further drawings. Preferred trans-sacral surgical access and TASIF pilot hole preparation tools are depicted in further drawings.

The lower regions of the spinal column comprising the coccyx, fused sacral vertebrae S1–S5 forming the sacrum, and the lumbar vertebrae L1–L5 described above are depicted in a lateral view in FIG. 1. The series of adjacent vertebrae located within the human lumbar and sacral spine have an anterior aspect, a posterior aspect and an axial aspect, and the lumbar vertebrae are separated by intact or damaged spinal discs labeled D1–D5 in FIG. 1. FIGS. 2 and 3 depict the posterior and anterior view of the sacrum and coccyx.

The method and apparatus for forming an anterior or posterior TASIF axial bore initially involves accessing an anterior sacral position, e.g. an anterior target point at the junction of S1 and S2 depicted in FIGS. 1 and 3, or a posterior sacral position, e.g. a posterior laminectomy site of S2 depicted in FIGS. 1 and 2. One (or more) visualized, imaginary, axial instrumentation/fusion line extends cephalad and axially in the axial aspect through the series of adjacent vertebral bodies to be fused, L4 and L5 in this illustrated example. The visualized AAIFL through L4, D4, L5 and D5 extends relatively straight from the anterior target point along S1 depicted in FIGS. 1 and 3, but may be curved as to follow the curvature of the spinal column in the cephalad direction. The visualized PAIFL extends in the cephalad direction with more pronounced curvature from the posterior laminectomy site of S2 depicted in FIGS. 1 and 2.

It should be noted that the formation of the anterior tract 26 through presacral space under visualization described above is clinically feasible as evidenced by clinical techniques described by J. J. Trambert, MD, in "Percutaneous Interventions in the Presacral Space: CT-guided Precoccygeal Approach—Early Experience (*Radiology* 1999; 213:901–904).

FIG. 6 depicts, in general terms, the surgical steps of accessing the anterior or posterior sacral positions illustrated in FIGS. 1–3 (S100) forming posterior and anterior TASIF axial bores (S200), optionally inspecting the discs and vertebral bodies, performing disc removal, disc augmentation, and vertebral bone reinforcement (S300), and implanting posterior and anterior spinal implants and rods (S400) in a simplified manner. In step S100, access to the anterior or posterior sacral position, that is the anterior target point of FIG. 3 or the posterior laminectomy site of FIG. 2 is obtained, and the anterior or posterior sacral position is penetrated to provide a starting point for each axial bore that is to be created. Then, an axial bore is bored from each point of penetration extending along either the PAIFL or AAIFL cephalad and axially through the vertebral bodies of the series of adjacent vertebrae and any intervertebral spinal discs (S200). The axial bore may be visually inspected using an endoscope to determine if the procedures of step S300 should be performed. Discoscopy or discectomy or disc augmentation of an intervening disc or discs or vertebroblasty of a vertebral body may be performed through the axial bore (S300). Finally, an elongated TASIF spinal implant or rod is inserted into each axial bore to extend cephalad and axially through the vertebral bodies of the series of adjacent vertebrae and any intervertebral spinal discs (S400). Other types of spinal implants for delivering therapies or alleviating pain as described above may be implanted in substitution for step S400.

Step S100 preferably involves creation an anterior or posterior percutaneous pathway that enables introduction of further tools and instruments for forming an anterior or posterior percutaneous tract extending from the skin incision to the respective anterior or posterior target point of the sacral surface or, in some embodiments, the cephalad end of a pilot hole over which or through which further instruments are introduced as described in the above-referenced '222 application. An "anterior, presacral, percutaneous tract" extends through the "presacral space" anterior to the sacrum. The posterior percutaneous tract or the anterior, presacral, percutaneous tract is preferably used to bore one or more respective posterior or anterior TASIF bore in the cephalad direction through one or more lumbar vertebral bodies and intervening discs, if present. A single anterior or posterior TASIF bore is preferably aligned axially with the respective visualized AAIFL or PAIFL, and plural anterior or posterior TASIF bores are preferably aligned in parallel with the respective visualized AAIFL or PAIFL. Introduction of spinal implants and instruments for performing discectomies and/or disc and/or vertebral body augmentation is enabled by the provision of the percutaneous pathway and formation of the anterior or posterior TASIF bore(s).

It should be noted that performing step S100 in the anterior and/or posterior TASIF procedures may involve drilling a pilot hole, smaller in diameter than the TASIF axial bore, that tracks the AAIFL and/or PAIFL in order to complete the formation of the anterior and/or posterior percutaneous tracts. Step S300 may optionally be completed through the AAIFL/PAIFL pilot hole following step S100, rather than following the enlargement of the pilot hole to form the TASIF axial bore in step S200.

The preferred embodiments of the present invention involve methods and apparatus including surgical tool sets for forming pilot holes or curved, posterior and anterior, TASIF axial bores 22 or 152 or $22_1 \ldots 22_n$, or $152_1 \ldots 152_n$ shown in FIGS. 4 and 5 in alignment with the curved, visualized AAIFL and PAIFL. The surgical tool sets comprise elongated drill shaft assemblies supporting distal boring tools, e.g., mechanical rotating drill bits, burrs, augurs, abraders, or the like (collectively referred to as boring heads or drill bits for convenience), that can be manipulated in use to form a selected curvature in a distal drill shaft segment and have sufficient torqueability to allow the user to rotate the curved distal segment into a desired boring plane from a proximal end of the elongated drill shaft assembly. When the distal segment is straightened, the drill bit bores straight ahead to bore a relatively straight section of the TASIF axial bore. Then, the distal segment is curved and urged into the desired boring plane so that the drill bit bores the next section of the TASIF axial bore at an angle to the previously bored caudal section of the TASIF axial bore resulting in an overall curvature in the TASIF axial bore aligned with the AAIFL or PAIFL.

A First Exemplary Boring Tool

Figure 9:
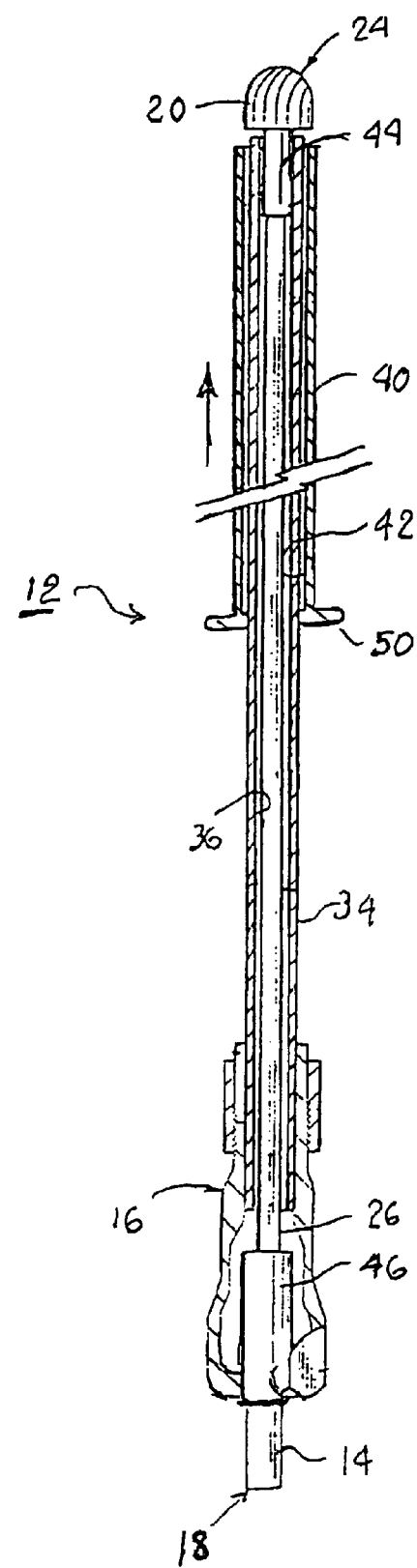
FIG. 9 is a cross-section view of the drill bit of FIGS. 7 and 8 with the curvature eliminated by full distal extension of the outer sheath to the distal end of the drill bit.

FIGS. 7–9 show one exemplary boring tool 10 for boring a single one or a plurality of curved anterior or posterior TASIF axial bores aligned with the curved, visualized AAIFL or PAIFL as illustrated in FIGS. 10–18. The boring tool comprises an elongated drill shaft assembly 12 and a drill motor 30 (shown in part) which may take any form. It will be understood that the drill motor 30 can be permanently attached to and form part of the proximal end of the elongated drill shaft assembly 12, but is depicted herein as a separate, detachable drill motor. The elongated drill shaft assembly 12 extends between an exposed proximal drive shaft end 14 at the proximal drill shaft assembly end 18 an exposed drill bit 20 at the distal drill shaft assembly end 24. The exposed proximal drive shaft end 14 is received within and attached to a chuck 32 of drill motor 30 in a manner well known in the art to rotate the drive shaft 26 extending from the drive shaft proximal end through the length of the elongated drill shaft assembly to the exposed distal drill bit 20. The exposed distal drill bit 20 may take any form of burr or auger or screw that can be rotated at a suitable speed to penetrate the dense and hard outer periostium and compact bone layers of the vertebral bodies and advance through the relatively softer, interiorly disposed, spongy bone. Then, the drill bit 20 is advanced in a curved path in the cephalad direction perforating each opposed face of each vertebral body and intervening disc while staying within the spongy bone of each vertebral body that is penetrated. The drill bit 20 is preferably radiopaque so that its advancement through vertebral bodies can be observed employing conventional imaging equipment.

The elongated drill shaft assembly 12 further comprises a pre-curved inner sheath 34 having an inner sheath lumen 36 receiving and enclosing the drive shaft 26, an outer sheath 40 having an outer sheath lumen 42 enclosing the inner sheath 34, and a housing 16 that is attached to the proximal end of the inner sheath 34. The outer sheath 40 can be retracted proximally over the inner sheath 34 so that a distal segment of the inner sheath 34 is exposed or extended distally over the inner sheath 34 so that the distal segment thereof is enclosed within the outer sheath lumen 42.

The drive shaft 26 is flexible and bendable and can formed of a single filament or multi-filar straight or coiled wire and is preferably radiopaque so that it can be observed using conventional imaging equipment. The distal end of the drive shaft 26 is attached to the drill bit 20 by in any manner, e.g., by welding to a proximal surface thereof or by being crimped inside a crimp tube lumen of a proximally extending crimp tube 44 of the drill bit 20 as shown in FIG. 9. The proximal end of the drive shaft 36 is received within a further crimp or weld tube 46 that extends distally from the proximal exposed drive shaft end 14 as shown in FIG. 9. The proximal exposed drive shaft end extends through a bearing in the proximal end wall of the housing 16 and is supported thereby for rotation by motor 30.

The outer diameters of the housing 16 and the drill bit 20 exceed the outer diameter of the straight outer sheath 40. The straight outer sheath 40 can be moved back and forth over the pre-curved inner sheath 34 between a proximal position depicted in FIG. 7, a distal position depicted in FIG. 9 and any number of intermediate positions bounded by the housing 16 and drill bit 20.

The straight outer sheath 40 is preferably formed of a stiff metal or plastic tube that is relatively stiffer and shorter in length than the more flexible, pre-curved inner sheath 34. The more flexible, pre-curved inner sheath 34 can be formed of a torqueable, plastic or metal, thin walled tubing and is pre-curved in a single plane to a suitable angle, e.g., about a 90° angle, in the distal segment thereof as shown in FIG. 7. The angle and radius of curvature of the distal segment can be selected along with the length and stiffness of the outer sheath 40 to meet the needs of tracking the AAIFL or the PAIFL. The stiffness of the outer sheath 40 is selected to enable it to be advanced distally to straighten the curvature of the distal segment of the inner sheath 34. However, the outer sheath 40 is flexible enough that it can be bent or curved within the confines of the curved TASIF axial bores as it is formed by the drill bit. In this way, the outer sheath can be advanced in the cephalad direction or retracted in the caudal direction and still conform to the curvature of the curved TASIF axial bore.

Posterior TASIF Axial Bore Formation

FIGS. 10–13 show steps included in step S200 for forming a posterior TASIF axial bore 22 through sacral and lumbar vertebrae and intervening discs axially aligned with the visualized PAIFL of FIGS. 1 and 2 using the boring tool of FIGS. 7–9. The same steps can be employed to form a pilot hole of step S100 that can be enlarged in step S200. Using this technique to form the posterior TASIF axial bore, a small diameter bore forming tool (e.g. 3.0 mm diameter) is used to first bore a small diameter curved pilot hole following the imaginary, visualized PAIFL 20 through S1, L5 and L4. Then, the boring tool is removed, and a guidewire having a threaded distal screw-in tip is advanced through the pilot hole and screwed into to the caudal end of the pilot hole and into cephalad portion of the L4 body. An over-the-wire bore enlarging tool having a flexible body capable of tracking the curved guidewire is fitted over the proximal end of the guidewire and manually or mechanically rotated and advanced along it. In this way, the small pilot hole diameter is enlarged to form the anterior TASIF axial bore 22 having a diameter e.g. a 10.0 mm diameter, and the enlarging tool is then removed.

It will be understood that the illustrated diameter of the posterior TASIF axial bore hole 22 relative to sizes of the vertebral bodies is merely exemplary, and that it is contemplated that the pilot hole and bore hole diameters can range from about 1–10 mm and 3–30 mm, respectively. Moreover, it will be understood that a plurality of such posterior TASIF axial bores $22_1 \ldots 22_n$ can be formed in side by side relation generally aligned with the PAIFL.

Figure 10:
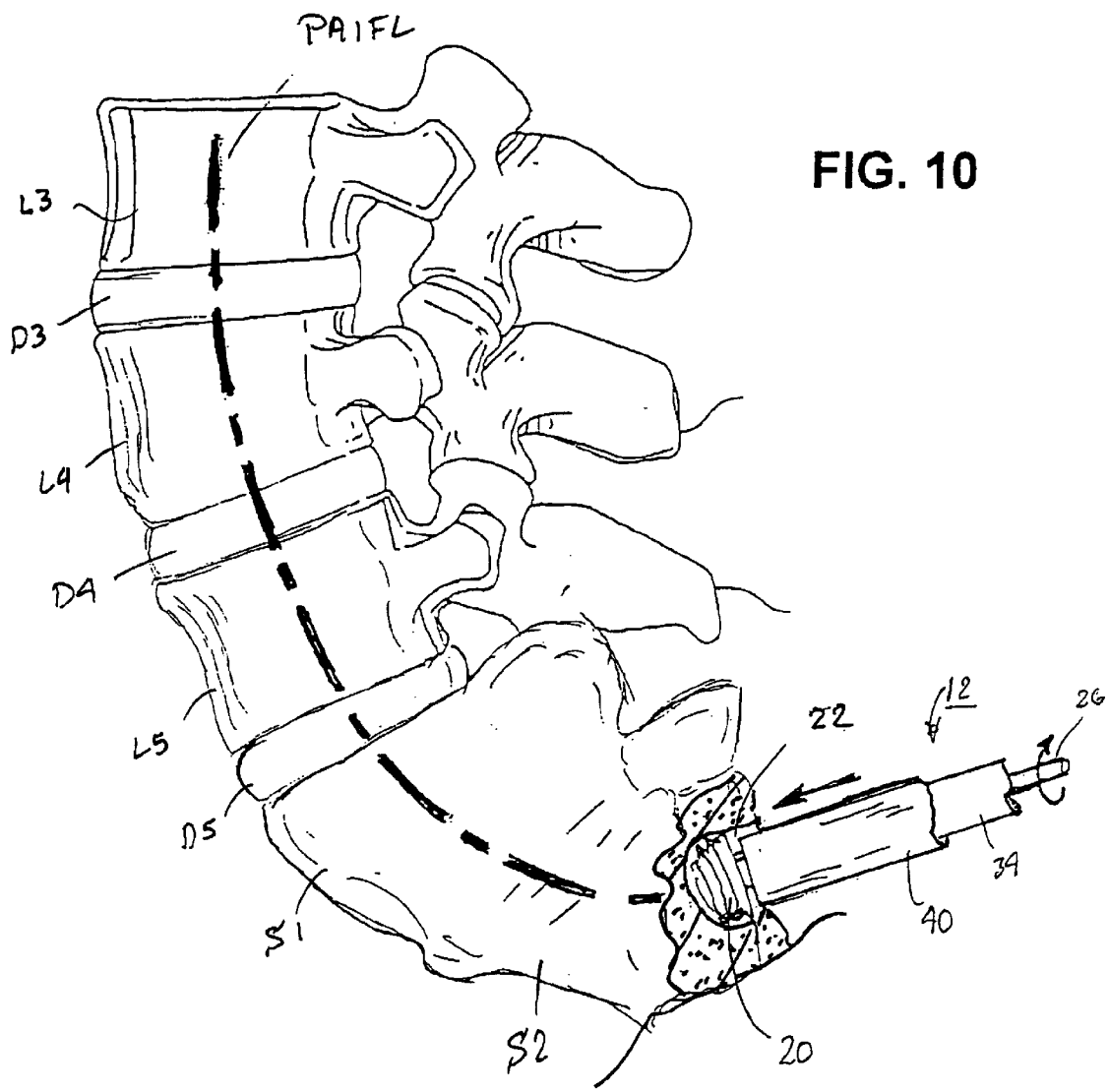
FIGS. 10–13 illustrate, in partial cross-section side views, one manner of forming a posterior TASIF axial bore through sacral and lumbar vertebrae and intervening discs axially aligned with the visualized PAIFL of FIGS. 1 and 2 using the boring tool of FIGS. 7–9.

In FIG. 10, the posterior surface of the sacrum is exposed in step S100 as described in the above-referenced '222 and '748 applications. The area of the patient's skin surrounding the incision site is surgically prepped, and the anus is excluded from the surgical field using adhesive drapes. The actual dermal entry site may be determined by the prone, preoperative CT scan or MRI study that maps the PAIFL. In step S100, an incision is made in the patient's skin over the posterior sacral surface of S2, and the subcutaneous tissue is separated to expose the posteriorly extending, bony ridge of the posterior sacral surface. A small laminectomy 14 is performed through the posterior ridge of the sacrum inferior. The thecal sac and nerve roots that are exposed by the laminectomy are gently retracted, and the terminal portion of the spinal canal is exposed.

The elongated drill shaft assembly 12 is axially aligned with the PAIFL at the posterior target point so that the initial penetration of the sacrum is substantially at right angles to the exposed sacral surface. A drill guide for receiving the drill drive shaft assembly for drilling or boring a TASIF axial bore from S2 along the visualized PAIFL 20 may optionally be attached to S2 and extended posteriorly through the exposed spinal canal and skin incision. In this starting position, the straight outer sheath 40 is fully distally extended to straighten the inner sheath 34, and the drill bit 20 is rotated to commence boring a posterior TASIF axial bore 22. The elongated drill shaft assembly 12 thus advances anteriorly to form a straight segment or section of the posterior TASIF axial bore 22.

Figure 11:
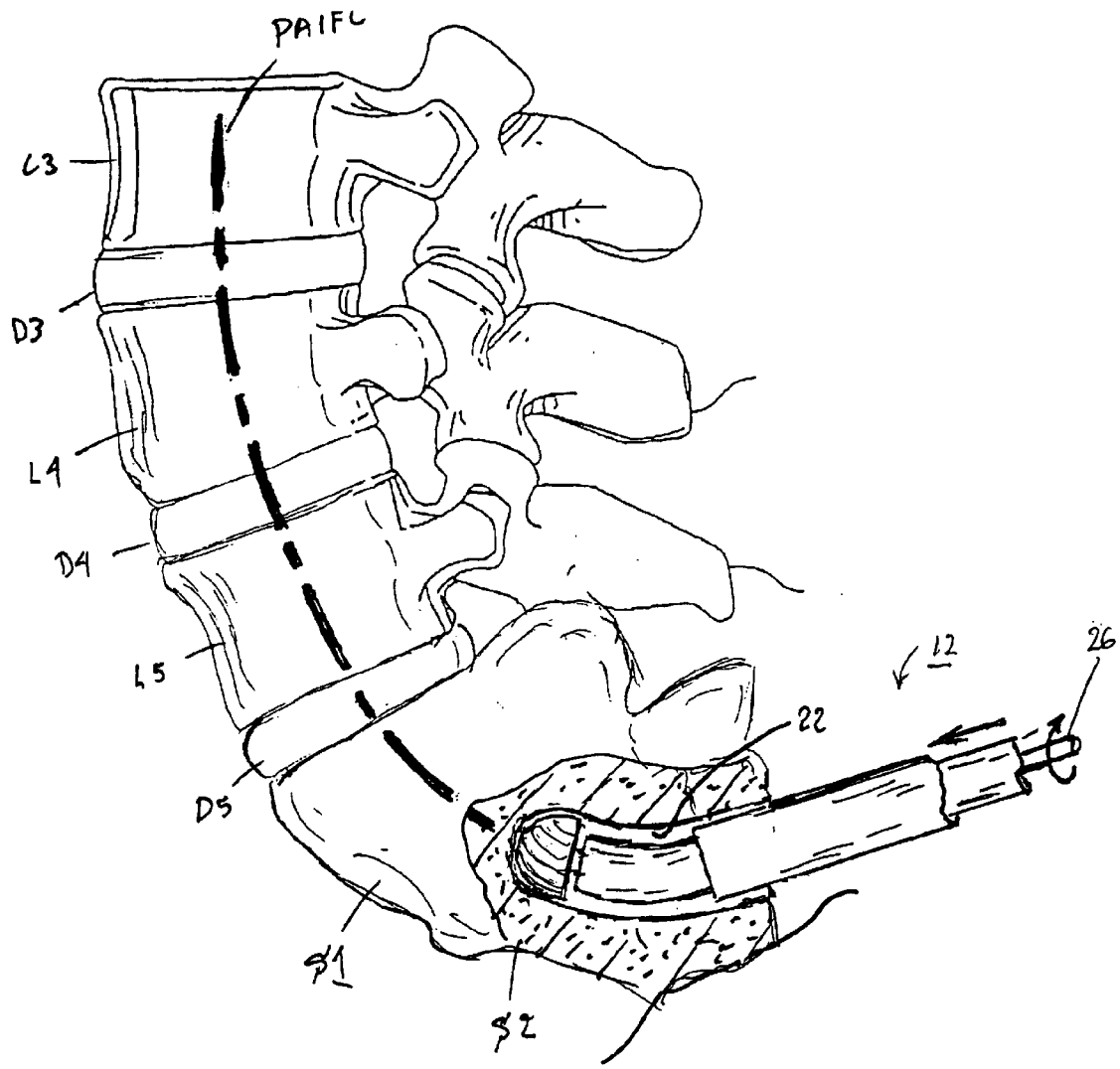
Figure 12:
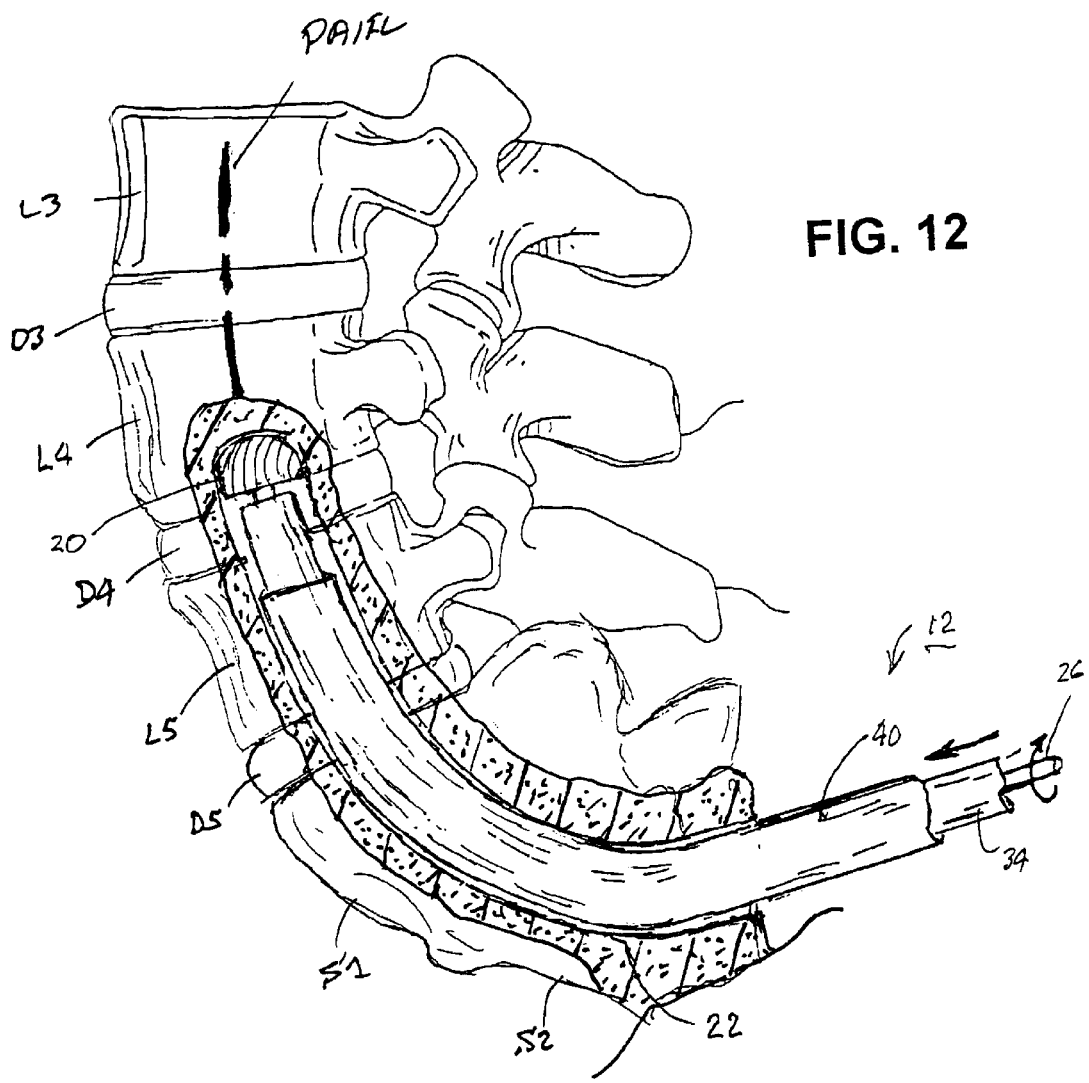
Figure 13:
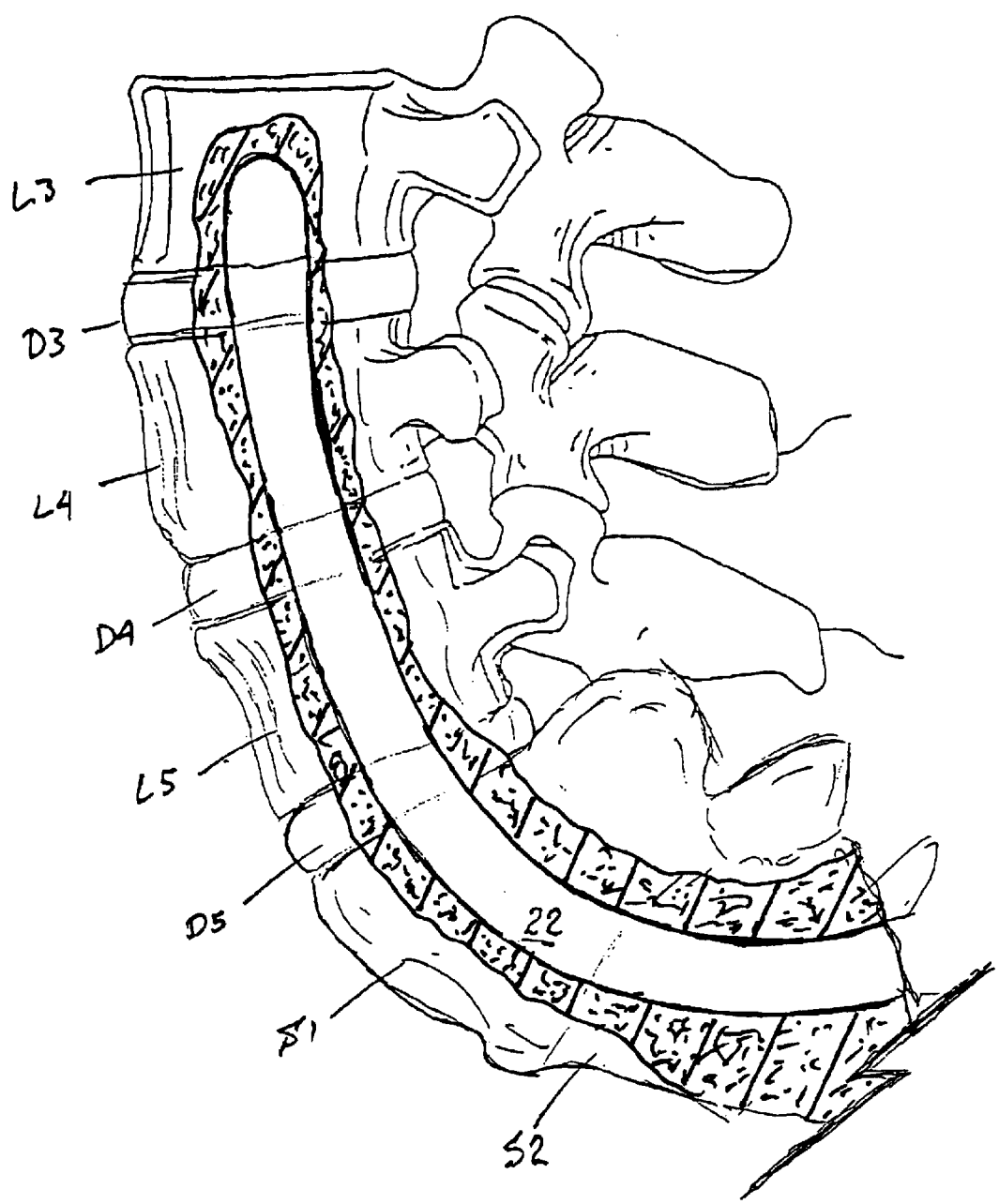

The progress of the drill bit 20 is observed using conventional imaging equipment. As the elongated drill shaft assembly 12 is extended anteriorly, it is necessary to retract the straight outer sheath 34 proximally to allow the inner sheath to curve in the cephalad direction to introduce a curvature in the cephalad segment of the posterior TASIF axial bore 22 as shown in FIG. 11. It is also necessary to orient and hold the proximal housing 16 so that the plane of curvature of the distal segment is aligned to the axis of the spine. This could be accomplished using external reference markings on the proximal housing 16. The degree of curvature of the cephalad segment of the posterior TASIF axial bore 22 is continually adjusted by incremental proximal and distal movements of the straight outer sheath 40 at flange 50 to expose more or less of the distal segment of the curved inner sheath 34 as shown in FIG. 12. In this way, the drill bit 20 advances through the sacral vertebrae in the cephalad direction and toward the lumbar vertebral bodies while staying within the spongy bone of each vertebral body. Theoretically, any number of vertebral bodies of the spine can be bored through in the cephalad direction.

Anterior TASIF Axial Bore Formation

Figure 14:
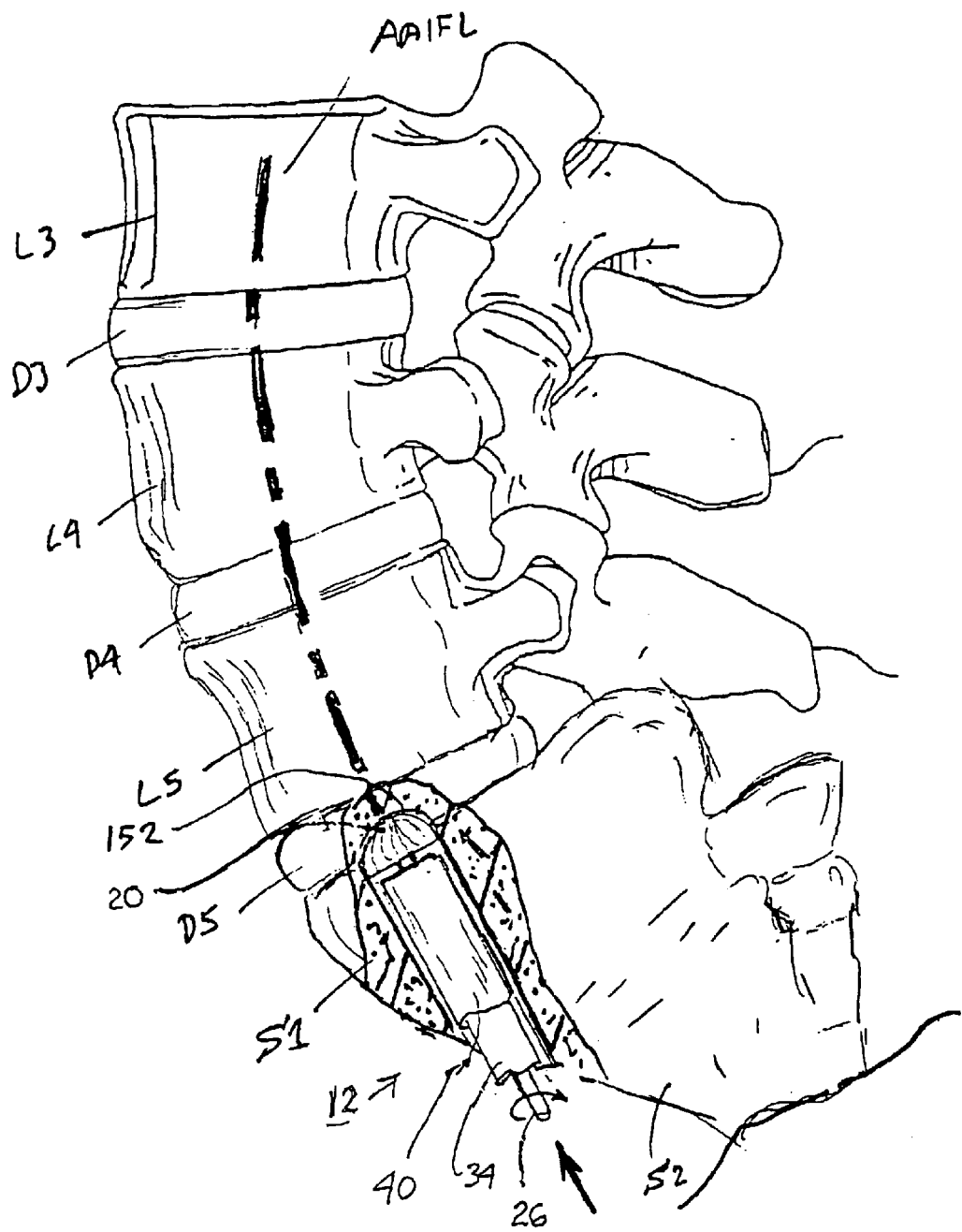
FIGS. 14–18 illustrate, in partial cross-section side views, one manner of forming an anterior TASIF axial bore through sacral and lumbar vertebrae and intervening discs axially aligned with the visualized AAIFL of FIGS. 1 and 2 using the boring tool of FIGS. 7–9.
Figure 15:
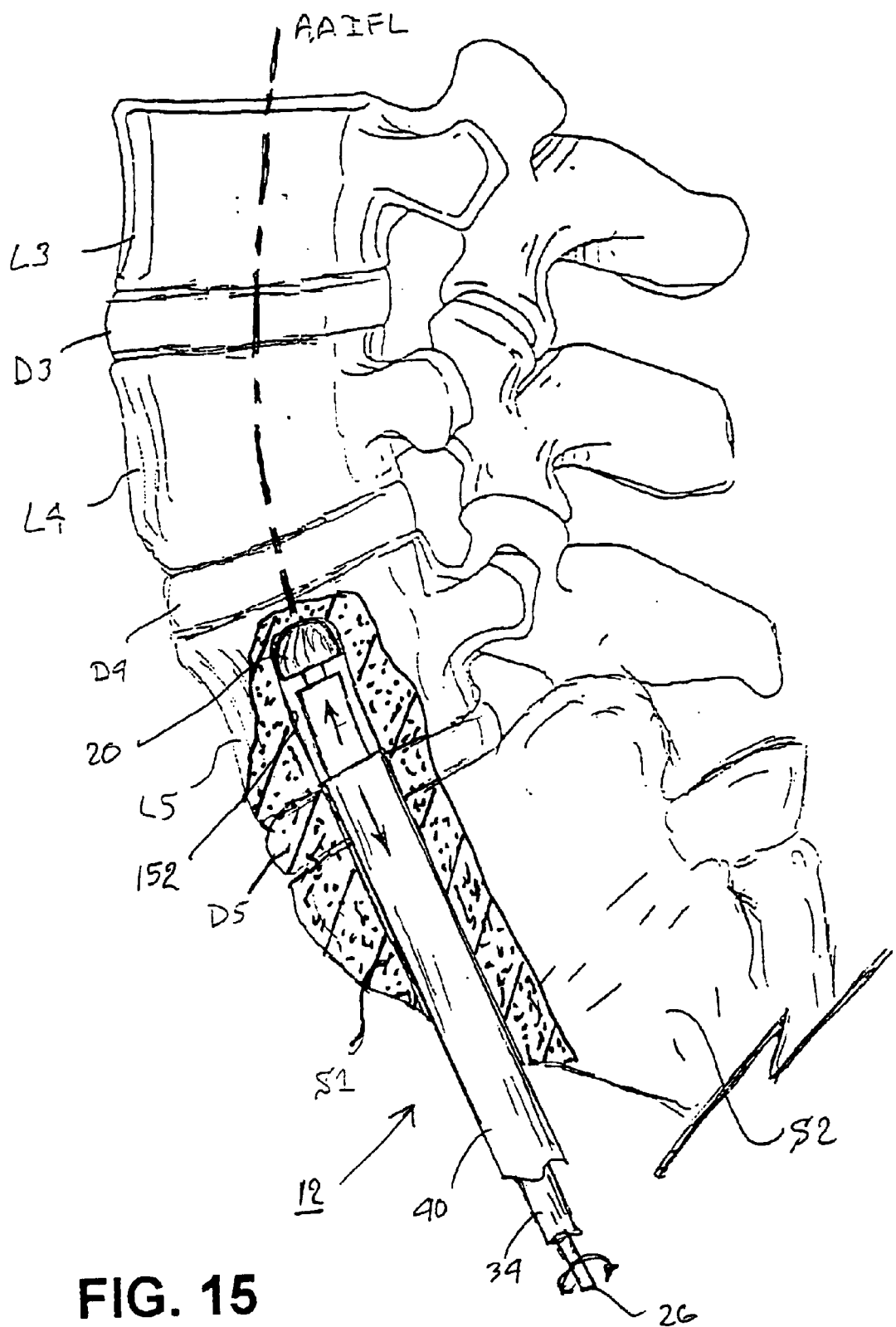
Figure 16:
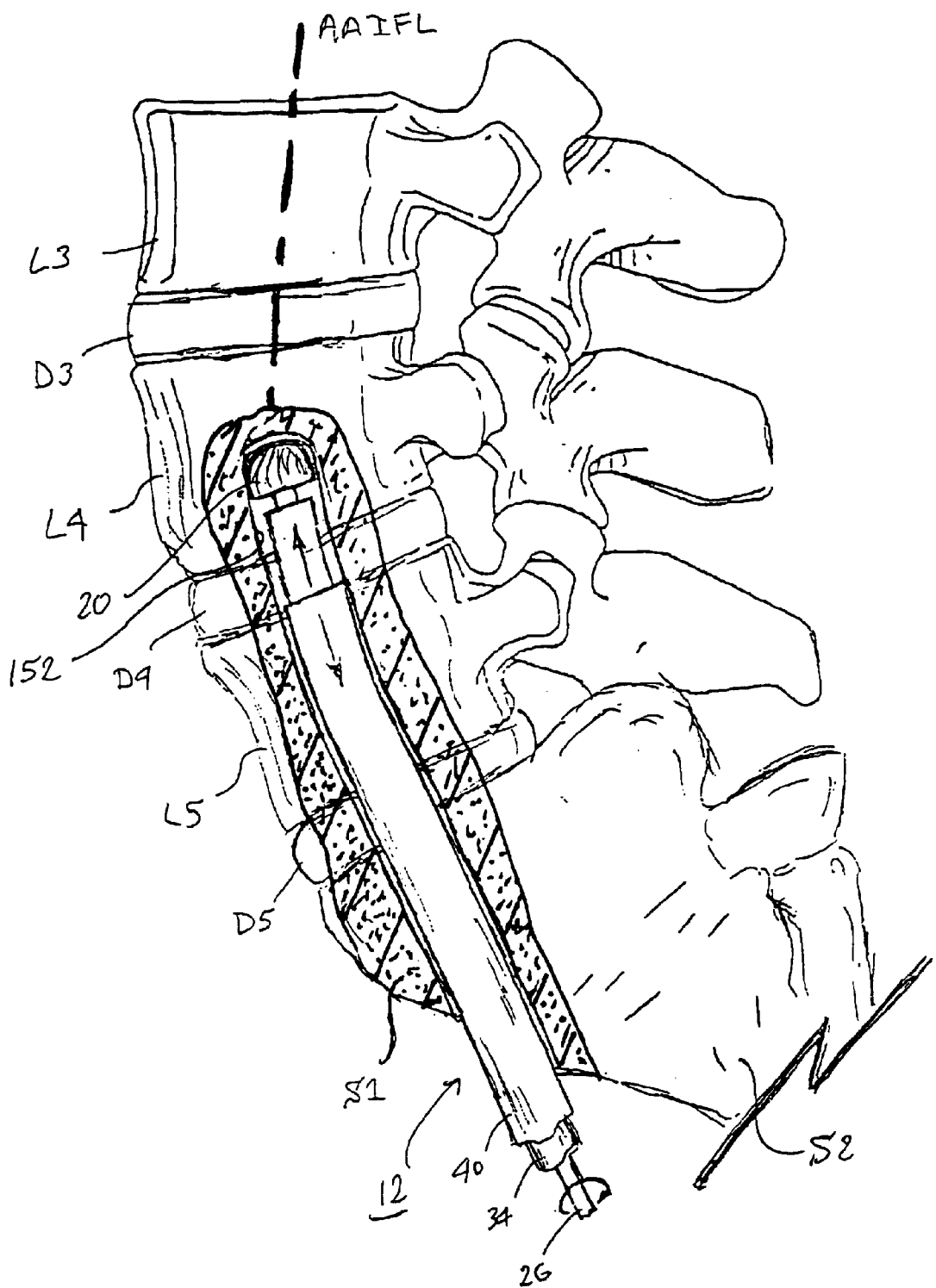

FIGS. 14–16 show steps included in step S200 for forming an anterior TASIF axial bore 152 through sacral and lumbar vertebrae and intervening discs axially aligned with the visualized AAIFL of FIGS. 1 and 2 using the boring tool of FIGS. 7–9. The same steps can be employed to form a pilot hole of step S100 that can be enlarged in step S200. It will be understood that the illustrated diameter of the anterior TASIF axial bore hole 152 relative to sizes of the vertebral bodies is merely exemplary, and that it is contemplated that the pilot holes and bore hole diameters can range from about 1–10 mm and 3–30 mm, respectively. Moreover, it will be understood that a plurality of such anterior TASIF axial bores $152_1 \ldots 152_n$ can be formed in side by side relation generally aligned with the AAIFL.

In FIG. 14, the elongated drill shaft assembly 12 is axially aligned with the AAIFL at the anterior target point so that the initial penetration of the sacrum is substantially at right angles to the opposed faces of S1 and L5 cephalad to the sacral surface of penetration. This anterior sacral surface starting point is accessed in step S100 from an incision in the patient's skin alongside the coccyx and via a percutaneous tract formed in the pre-sacral space which may or may not include a tract forming structure or tool as disclosed in the above-referenced '222 and '748 applications.

In this starting position, the straight outer sheath 40 is either fully distally extended to straighten the inner sheath 34 or retracted slightly depending on the patient's anatomy to provide an optimal orientation to the AAIFL. The drill bit 20 is rotated to commence boring an anterior TASIF axial bore 152, and the elongated drill shaft assembly 12 advances anteriorly to form a relatively straight or slightly curved segment of the posterior TASIF axial bore 22.

Again, the progress of the drill bit 20 is observed using conventional imaging equipment. As the elongated drill shaft assembly 12 is extended in the cephalad direction through S1, D5 (if present) and L5, it becomes necessary to retract the straight outer sheath 34 proximally to allow the inner sheath to curve in the cephalad direction to introduce a greater degree of curvature in the cephalad segment of the anterior TASIF axial bore 152 as shown in FIG. 15. Again, it is also necessary to orient and hold the proximal housing 16 so that the plane of curvature of the distal segment is aligned to the axis of the spine. The degree of curvature of the cephalad segment of the anterior TASIF axial bore 152 is continually adjusted by incremental proximal and distal movements of the straight outer sheath 40 at flange 50 to expose more or less of the distal segment of the curved inner sheath 34 as shown in FIG. 15. In this way, the drill bit 20 advances through the sacral vertebrae in the cephalad direction and through the lumbar vertebral bodies while staying within the spongy bone of each vertebral body.

Figure 17:
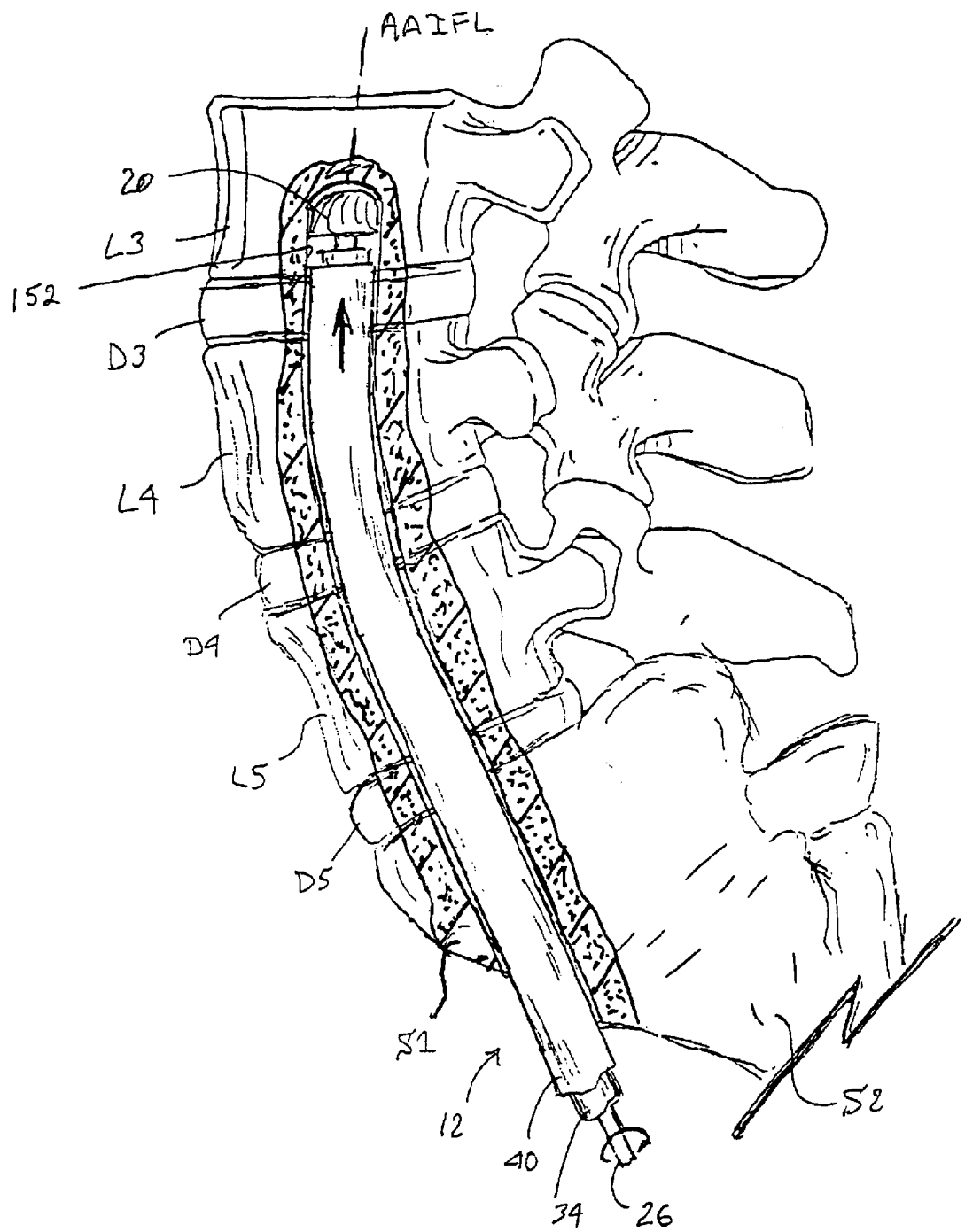
Figure 18:
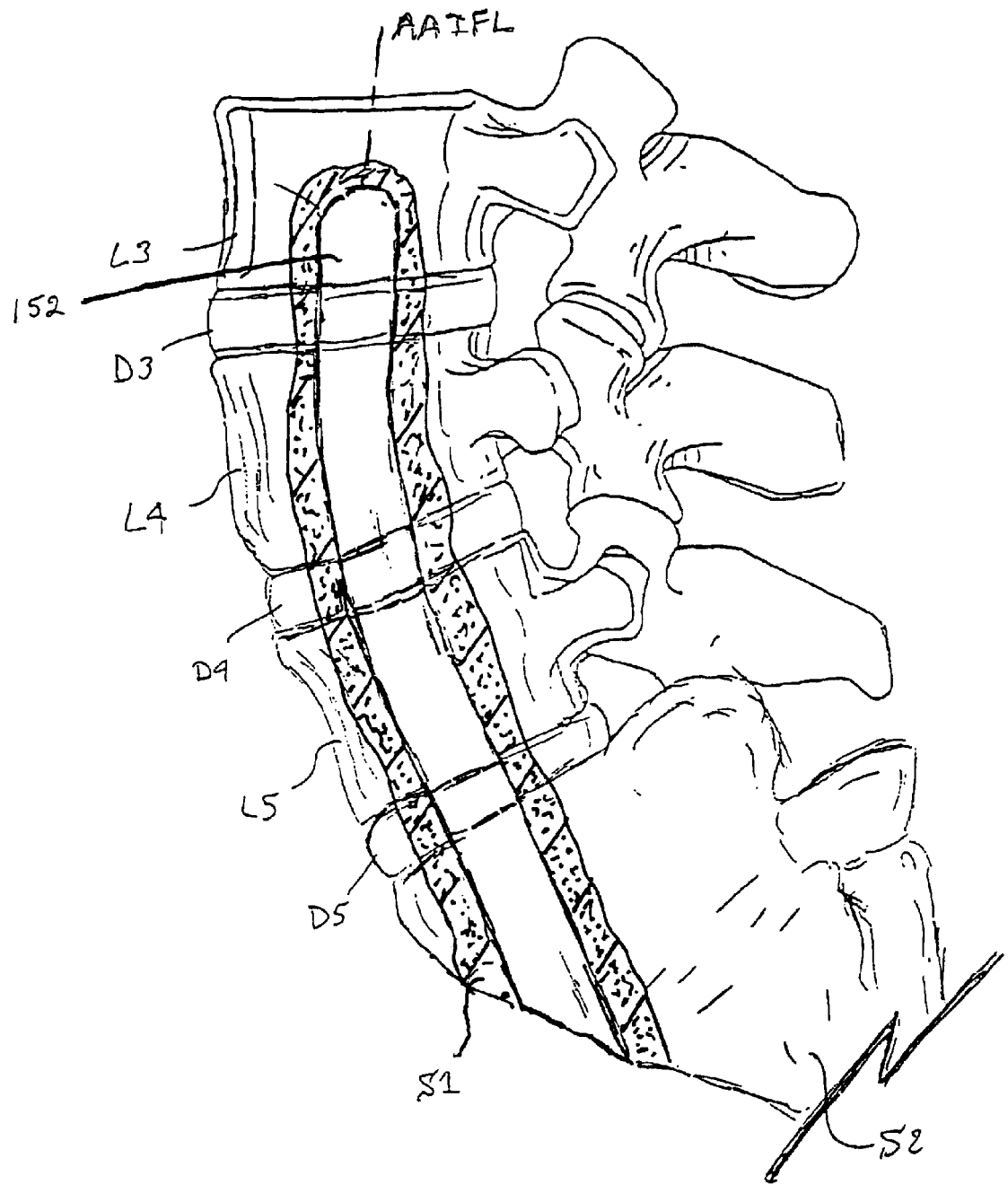
Figure 22:
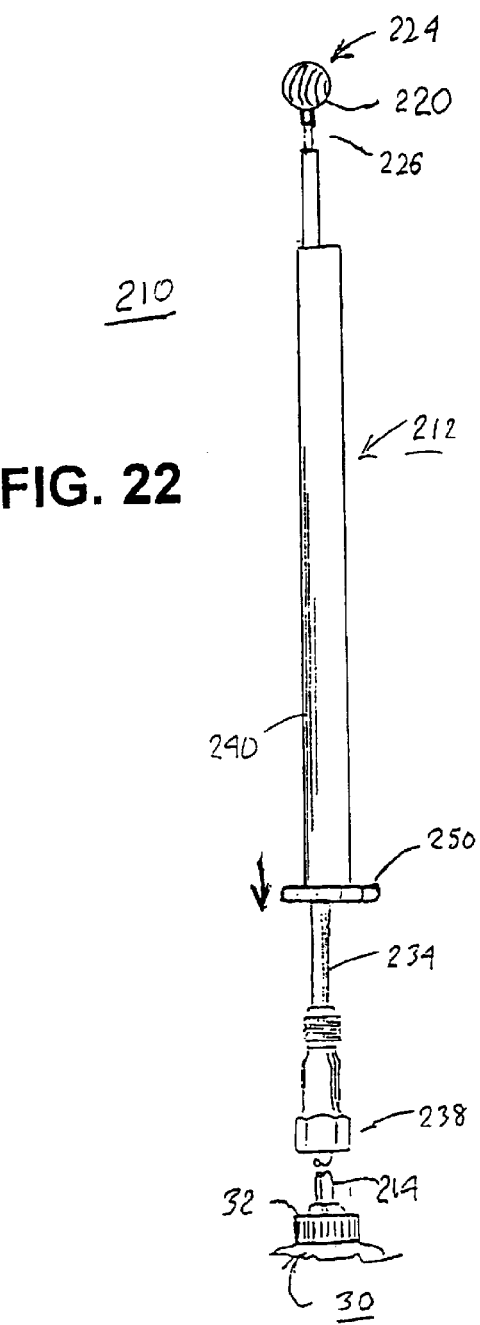

Slight but abrupt angular changes in the overall curvature of the anterior TASIF axial bore 152 are made within the vertebral bodies of L5 and L4 as shown in FIGS. 15 and 16, by caudal retraction of the outer sheath 40 and cephalad advancement of inner sheath 34. It is expected that it will usually be easier to adjust the angle of the drill bit 20 within the spongy bone interior to the vertebral bodies than in the disc space or while boring through the harder exterior vertebral bone. Therefore, after the spongy interior bone is bored through, the outer sheath 40 is advanced in the distal direction to straighten the angle of advancement of the drill bit 20 through the harder vertebral bone on either side of the disc. This straightened boring angle of attack is shown in FIG. 17, for example, where the drill bit 20 is advanced across the opposed faces of vertebral bodies L4 and L5 with the outer sheath 40 fully advanced in the cephalad direction. This process results in short relatively straight sections separated by more curved sections of the of the anterior TASIF axial bore 152. Thus, the resulting anterior TASIF axial bore 152 shown in FIG. 18 exhibits an overall curvature tracking the spinal curvature and the visualized AAIFL, but the curve radius varies, showing a shorter radius within the central portions of vertebral bodies L5 and L4.

A Further Exemplary Boring Tool

FIGS. 19–21 illustrate a further embodiment of an exemplary boring tool 110 comprising a drill motor 30 and an elongated drill shaft assembly 112 employing one or more tip deflection wire 104 (FIG. 21) for imparting a desired curvature in the distal segment of sheath 134. The sheath 134 extends from the distal end 124 into the housing 124 in the manner of sheath 34 depicted in FIG. 9, but it encloses an inner lumen 136 for receiving the drive shaft 126 and a radially offset tip deflection wire lumen 102 receiving a tip deflection wire 104. The distal end of the drive shaft 126 is attached to the drill bit 120 in the manner described above for attachment of the distal end of drive shaft 26 with the drill bit 20. The proximal end of the drive shaft 126 is attached to the proximal exposed drive shaft end 114 in the manner that the proximal end of the drive shaft 26 is attached to the proximal exposed drive shaft end 14. The drive shaft 126 may take any form including the depicted coiled wire form with or without a core wire extending through the coiled wire lumen.

The tip deflection wire 104 extends through the pull wire lumen extending along one side of the inner drive shaft sheath 134 between an attachment point at the distal end 124 and an attachment within housing 138 with distal segment curvature control ring 106 mounted on housing 138. The distal segment of drive shaft sheath 134 distal to junction 136 is more flexible than the proximal segment of drive shaft sheath 134 proximal to junction 136. The distal segment curvature control ring 106 is located over the cylindrical surface of housing 138, and an inwardly extending member extends into an elongated groove 108 in the housing 138 where it is attached to the proximal end of the tip deflection wire 104. The retraction of tip deflection wire 104 to form the curves in the drive shaft distal segment depicted in FIGS. 19 and 20 is effected by sliding the control ring 106 proximally from a rest or neutral position wherein the distal segment assumes a straight distal segment shape 1' as depicted in broken lines in FIG. 19. It will be understood that the length of the distal segment of the drive shaft 126 and the range of motion of the control ring 106 from the neutral position can be selected so as to form any angle or range of curvature that may be found desirable. Furthermore, it will be understood that the range of motion of the control ring 106 from the neutral position can be selected such that the control ring may be pushed distally from the neutral position to impart a curvature in the distal segment that is opposite to the curvatures depicted in FIGS. 19 and 20. The tip deflection wire 104 can therefore be either a pull wire for retraction only or a tip deflection wire for retraction and extension.

The boring tool 110 can be employed to form the posterior and anterior TASIF axial bores 22 and 152 or a plurality of the same in the same manner as described above with respect to FIGS. 10–18. The curvature of the posterior and anterior TASIF axial bores 22 and 152 is controlled by manipulation of the distal segment curvature control ring 106 as the drill bit 120 is advanced in the cephalad direction from the starting points depicted in FIGS. 10 and 14.

A Still Further Exemplary Boring Tool

FIGS. 22–25 illustrate a further embodiment of an exemplary boring tool 210 comprising a drill motor 230 and an elongated drill shaft assembly 212. The elongated drill shaft assembly 212 further comprises a straight inner sheath 234 having an inner sheath lumen 236 receiving and enclosing the drive shaft 226, a straight outer sheath 240 having an outer sheath lumen 242 enclosing the inner sheath 234, and a housing 238 that is attached to the proximal end of the inner sheath 234. In this embodiment, the inner sheath 234 is optional and can be eliminated to reduce the overall diameter of the elongated drill shaft assembly 212.

The drive shaft 226 is flexible and bendable enough to be either be straight when extended distally or curved in use as described below and can formed of a single filament or multi-filar straight or coiled wire that is preferably radiopaque so that it can be observed using conventional imaging equipment. The distal end of the drive shaft 226 is attached to the spherical drill bit 220 by in any manner, e.g., by welding to a proximal surface thereof or by being crimped inside a crimp tube lumen of a proximally extending crimp tube 244 of the drill bit 220 as shown in FIG. 23. The proximal end of the drive shaft 236 is received within a further crimp or weld tube 246 that extends distally from the proximal exposed drive shaft end 214 as shown in FIG. 23. The proximal exposed drive shaft end 214 extends through a bearing in the proximal end wall of the housing 238 and is supported thereby for rotation by motor 30.

The flexible outer sheath 240 is generally circular in cross-section and extends between a push-pull proximal handle 250 and a distal end thereof. The outer sheath lumen 242 is radially offset from the axis of the flexible outer sheath 240 so that the drill shaft 226 and optional inner sheath 234 extend through the outer sheath lumen to locate the drill bit 220 offset from the axis of the flexible outer sheath 240 as shown in FIGS. 23 and 24. A sleeve-shaped, thrust bearing 228 formed of a hard plastic or metal material is disposed in the outer sheath distal end surrounding the distal end opening of the outer sheath lumen 242 and projecting slightly distally therefrom. The remaining exposed portion of the outer sheath 240 is flexible and compressible to be advanced through a bore hole formed by the drill bit 220. The outer diameters of the housing 238 and the drill bit 220 exceed the outer diameter of the flexible outer sheath 240. The flexible outer sheath 240 can be moved back and forth over the inner sheath 234 between a proximal position depicted in FIG. 22 and a distal position depicted in FIG. 25. The outer diameter of the drill bit 220 is approximately equal to or slightly larger than the outer diameter of the outer sheath 240 as shown in FIGS. 23 and 24.

Figure 25:
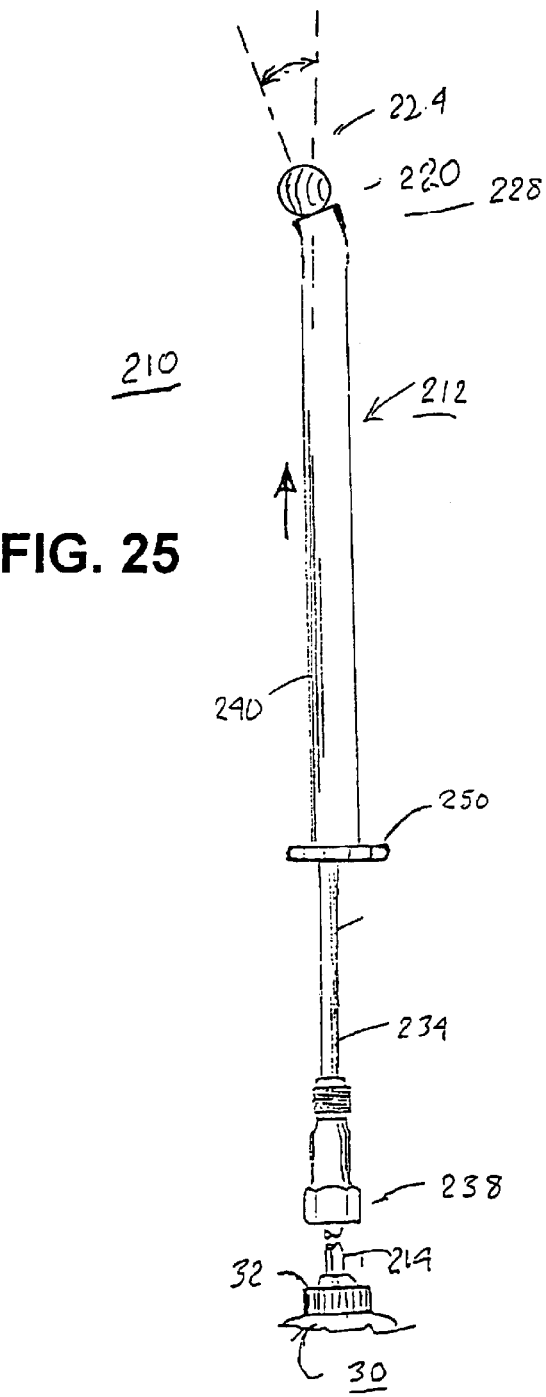

A curvature in the distal segment of the outer and inner sheaths 240 and 234 toward the radial offset direction D (FIG. 23) is formed when the outer sheath 240 is advanced distally to its full extent as shown in FIG. 25. The distal surface of the thrust bearing 228 bears against the proximal spherical surface of the drill bit 220 when force is applied by pushing the outer sheath 240 distally at handle 250 and/or pulling the inner sheath 234 proximally at housing 238. The axial offset of the outer sheath lumen 242 and the flexibility of the outer sheath 240 just proximally to thrust bearing 228 cooperate to laterally deflect the drill bit 220 toward the radial offset direction D. The thinner wall of the outer sheath 240 in the radial offset direction contributes to its axial compression and inducement of the depicted curvature. It will be understood that the angular deflection of the drill tip 220 and the range of curvature of the distal segment of the outer and inner sheaths 240 and 234 toward the radial offset direction D can be selected by the selection of materials and the offset of the outer sheath lumen 242 from the axis of outer sheath 240.

The boring tool 210 can be employed to form the posterior and anterior TASIF axial bores 22 and 152 or a plurality of the same in the same manner as described above with respect to FIGS. 10–18. The curvature of each section of the posterior and anterior TASIF axial bores 22 and 152 is controlled by proximal and distal manipulation of the outer sheath 240 with respect to inner sheath 234 as the drill bit 220 is advanced in the cephalad direction from the starting points depicted in FIGS. 10 and 14.

It will be understood that the above-described embodiments of TASIF axial bore or pilot hole boring tools can be modified in many ways. For example, the elongated drive shaft assemblies can be modified to provide fluid lumens for pumping flushing fluids into the TASIF axial bores at the distal ends thereof and for conveying flushing fluid and bone fragments proximally to the exterior of the patient's body. Also, the elongated drive shaft assemblies and drill bits can be modified to provide a guide wire lumen extending from the proximal to the distal ends thereof for advancement over a guidewire. Suitable drive motors for rotating a drive shaft over a guidewire and drive shaft assemblies having flushing capabilities are disclosed in U.S. Pat. No. 6,066,152, for example.

When a single posterior or anterior TASIF axial bore 22 or 152 is formed, it can be formed in axial or parallel alignment with the visualized axial AAIFL and PAIFL as described. Similarly, multiple posterior or anterior TASIF axial bores can be formed all in parallel alignment with the visualized axial AAIFL and PAIFL or with at least one such TASIF axial bore formed in axial alignment with the visualized axial AAIFL and PAIFL.

Diverging TASIF Axial Bores

Moreover, multiple anterior or posterior TASIF axial bores can be formed all commencing at an anterior or posterior target point of FIGS. 1–3 and extending in the cephalad direction with each TASIF axial bore diverging apart from the other and away from the visualized axial AAIFL and PAIFL. The diverging TASIF axial bores terminate as spaced apart locations in a cephalad vertebral body or in separate cephalad vertebral bodies.

Figure 26:
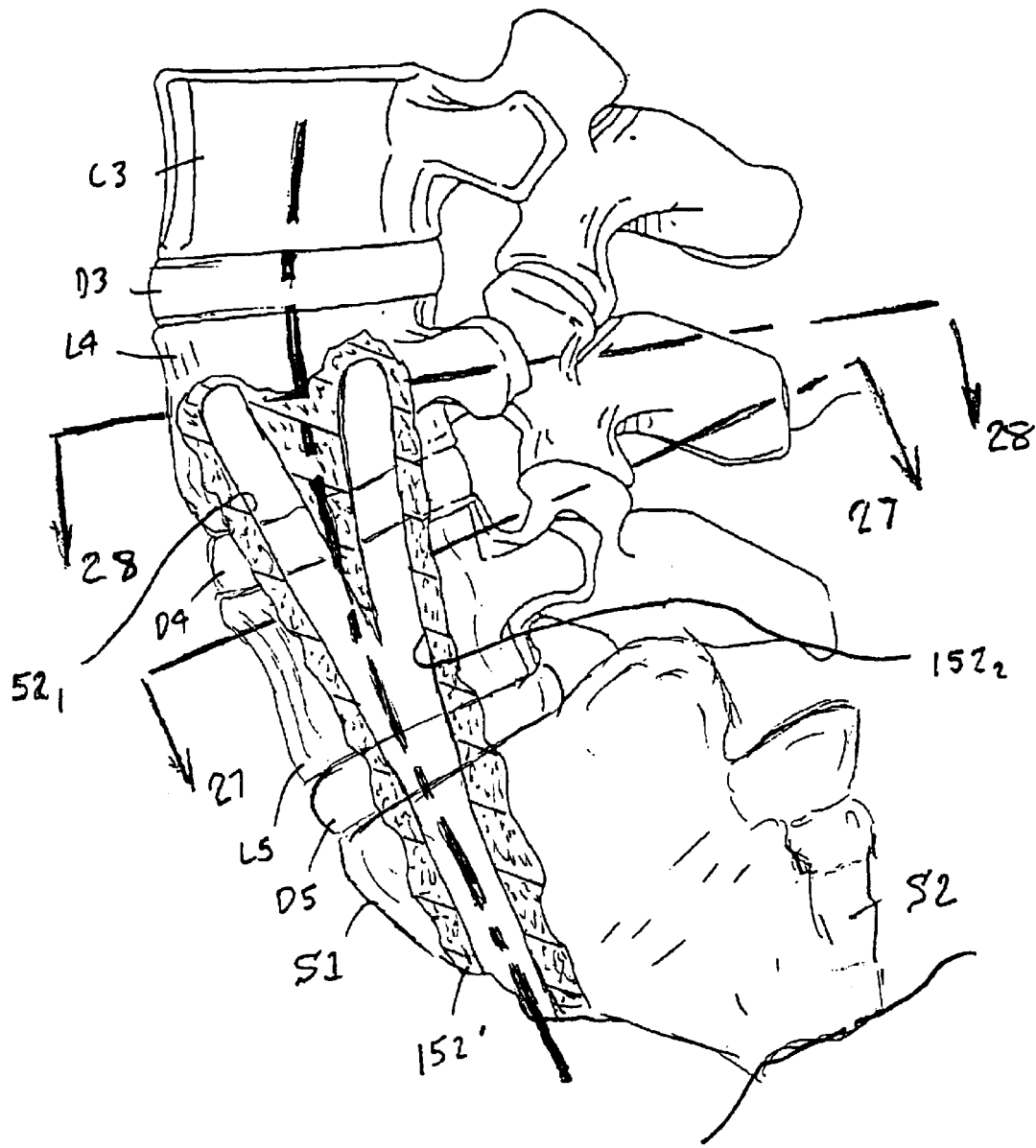
FIG. 26 depicts, in a partial cross-section side view, the formation of a plurality of curved TASIF axial bores that diverge apart from a common caudal section in the cephalad direction.
Figure 27:
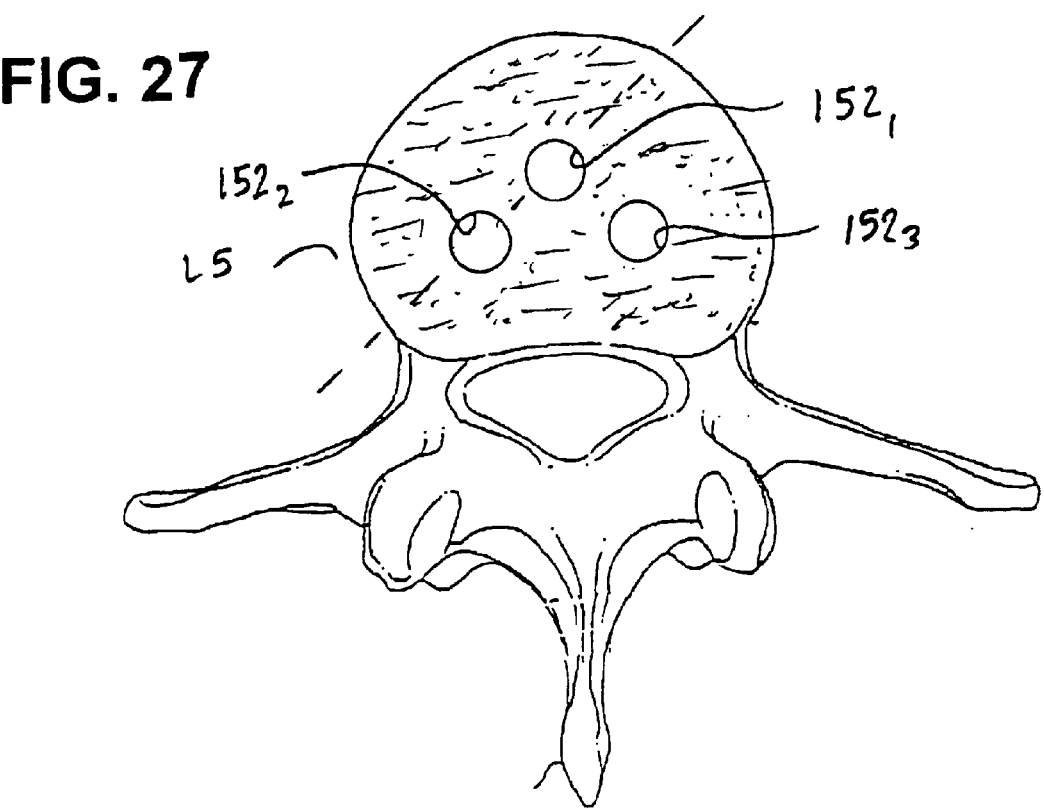
FIGS. 27 and 28 depict, in partial cross-section end views taken along lines 27—27 and 28—28, respectively, of FIG. 26, the divergence of the plurality of curved TASIF axial bores.
Figure 28:
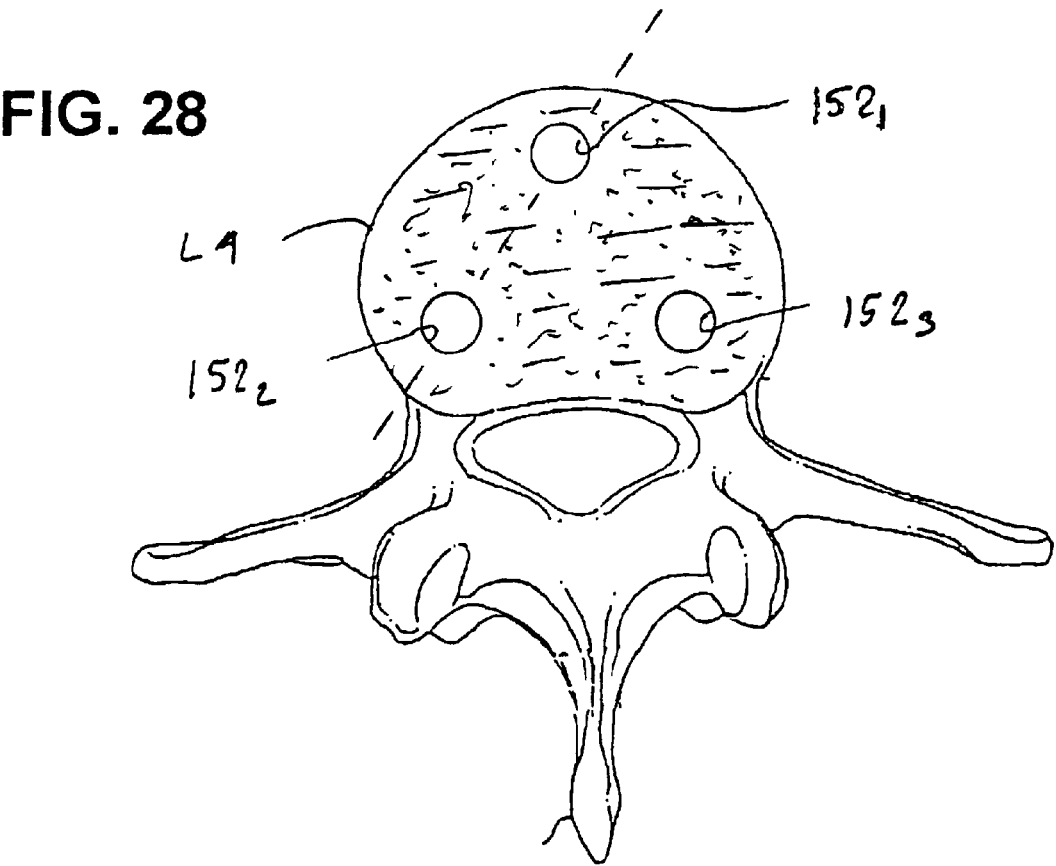

For example, FIGS. 6–27 depict a group of three anterior TASIF axial bores $152_1$, $152_2$, $152_3$ that are bored from a common caudal entrance bore section 152' starting at the anterior target point and extending in the cephalad direction generally following the curvature of the AAIFL but diverging outwardly. the divergence from the common entry bore section can start in the sacral vertebra or in L5 or in L4 or in any other cephalad vertebra that the bore extends into or through. A "tripod" of the diverging TASIF axial bores $152_1$, $152_2$, $152_3$ is formed as shown in FIGS. 26 and 27. The common caudal entrance bore section 152' through S1, and traversing disc D5 and part of L4 can be larger in diameter than the diverging TASIF axial bores $152_1$, $152_2$, $152_3$ to accommodate the insertion of three elongated spinal implants therein. It is believed that the insertion of elongated spinal implants within the "tripod" of the diverging TASIF axial bores $152_1$, $152_2$, $152_3$ can substantially strengthen and enhance fusion of L4, L5 and S1. The diverging TASIF axial bores $152_1$, $152_2$, $152_3$ can be extended further than shown in FIGS. 25–27.

Summary

Thus, the above described tool sets can be employed to bore a curved trans-sacral axial bore or pilot hole in alignment with the visualized AAIFL or PAIFL cephalad and axially through the vertebral bodies of a series of adjacent vertebrae and any intervertebral spinal discs without unintentially perforating through a side of a vertebra. The alignment can be axial alignment as shown in FIG. 4, or parallel alignment as shown in FIG. 5 or diverging alignment as shown in FIGS. 25–27. In use, the boring head is angled at a selected boring angle, e.g., by inducing a selected curvature in the distal segment of a sheath surrounding the drive shaft, and the boring plane of the angled boring head is oriented, e.g., by rotating the proximal housing and sheath to rotate the elongated drill shaft assembly, as is found necessary to obtain the desired bore curvature and alignment in any given case.

The curved, posterior and anterior TASIF axial bores 22 and 152 that are formed in step S200 of FIG. 6 as described above start in the sacrum at the respective posterior and anterior target points and extend upwardly or cephalad through the vertebral body of S1 or S2 and through the cephalad vertebral bodies including L5 and L4 and the intervening discs denoted D4 and D5 in FIG. 1. Discs D4 and D5 are usually damaged or have degenerated between lumbar spine vertebrae and cause the pain experienced by patients requiring intervention and fusion of the vertebrae. An inspection of the vertebral bodies and discs along the sides of the posterior or anterior TASIF axial bore 22 or 152 can be made using an elongated endoscope inserted therethrough (or through a pilot hole if one is formed earlier). A discectomy or disc augmentation and/or vertebroblasty may be performed pursuant to step S300 of FIG. 6 through the posterior or anterior TASIF axial bore 22 or 152 to relieve the patients symptoms and aid in the fusion achieved by insertion of a spinal implant. In such procedures, materials or devices can be inserted through the curved, posterior and anterior TASIF axial bores 22 and 152 to fit into excised disc space or damaged vertebral bodies.

It will be understood that various types of axial spinal implants can be inserted into the above-described curved, posterior and anterior TASIF axial bores 22 and 152. Such axial spinal implants can be combined with laterally installed disc replacements or spacers.

All patents and other publications identified above are incorporated herein by reference.

While the present invention has been illustrated and described with particularity in terms of preferred embodiments, it should be understood that no limitation of the scope of the invention is intended thereby. The scope of the invention is defined only by the claims appended hereto. It should also be understood that variations of the particular embodiments described herein incorporating the principles of the present invention will occur to those of ordinary skill in the art and yet be within the scope of the appended claims.

What is claimed is:

1. A method for providing access to a series of adjacent vertebrae located within a human lumbar and sacral spine having an anterior aspect, a posterior aspect and an axial aspect, wherein the axial aspect is curved in the posterior-anterior plane due to curvature of the spinal column, the vertebrae separated by intact or damaged spinal discs, the method comprising the steps of:
   accessing an anterior or posterior sacral target point of a sacral vertebra in alignment with a visualized, curved axial instrumentation/fusion line extending in said axial aspect through the series of adjacent vertebral bodies; and
   from the accessed sacral target point, boring a curved trans-sacral axial bore in alignment with said axial instrumentation/fusion line cephalad and axially through the vertebral bodies of said series of adjacent vertebrae and any intervertebral spinal discs;
   wherein the boring step further comprises the steps of:
      providing a boring assembly comprising a boring head capable of being imaged at the distal end of a flexible boring drive shaft and a directional control mechanism for adjusting a boring angle of the boring head;
      imaging the boring head and the vertebrae;
      while observing the imaged boring head and vertebrae, advancing the boring head from the anterior or posterior target point through the vertebral bodies and any intervening discs; and
      during advancement, adjusting the boring angle of the boring head to form a curve in the axial bore;
      wherein the step of adjusting the boring angle includes advancing or retracting a sheath relative to said boring head.

2. The method of claim 1, wherein the adjusting step further comprises the steps of:
   straightening the boring angle of the boring head when boring through opposed end faces of facing vertebral bodies and the intervening disc space so that the axial bore is aligned axially normal to the opposed end faces of the facing vertebral bodies; and
   deflecting the boring angle of the boring head when boring within a vertebral body between the end faces of the vertebral body, whereby the curved axial bore can be formed of relatively straight and curved sections.

3. A method for providing access to a series of adjacent vertebrae located within a human lumbar and sacral spine having an anterior aspect, a posterior aspect and an axial aspect, wherein the axial aspect is curved in the posterior-anterior plane due to curvature of the spinal column, the vertebrae separated by intact or damaged spinal discs, the method comprising the steps of:
   accessing an anterior or posterior sacral target point of a sacral vertebra in alignment with a visualized, curved axial instrumentation/fusion line extending in said axial aspect through the series of adjacent vertebral bodies; and
   from the accessed sacral target point, boring a curved trans-sacral axial bore in alignment with said axial instrumentation/fusion line cephalad and axially through the vertebral bodies of said series of adjacent vertebrae and any intervertebral spinal discs;
   wherein the boring step further comprises the steps of:
      providing a boring assembly comprising a boring drill bit capable of being imaged at the distal end of a flexible drive shaft, the drive shaft coupled at a drive shaft proximal end to a drill motor and at a drive shaft distal end to the drill bit, whereby the drill bit and drive shaft are rotatable by operation of the drill motor, a flexible inner sheath having an inner sheath lumen through which said drive shaft extends said inner sheath having a curved distal segment, and a straight flexible outer sheath having an outer sheath lumen through which said inner sheath extends, the outer and inner sheaths providing directional control to the boring angle of the drill bit by selectively distally advancing or proximally retracting the outer sheath over or from a distal segment of the inner sheath; and
      operating the drill motor and advancing the drill bit from the anterior or posterior target point while adjusting the boring angle of the drill bit by selectively advancing or retracting the outer sheath over or from the distal segment of the inner sheath to drill the axial bore through the vertebral bodies and any intervening discs in alignment with the axial instrumentation/fusion line.

4. The method of claim 3, wherein the adjusting step further comprises the steps of:

straightening the boring angle of the drill bit when boring through opposed end faces of facing vertebral bodies and the intervening disc space by extending the outer sheath distally over the inner sheath so that the axial bore is aligned axially normal to the opposed end faces of the facing vertebral bodies by advancing the outer sheath distally over the drive shaft; and deflecting the boring angle of the drill bit when boring within a vertebral body between the end faces of the vertebral body by retracting the outer sheath proximally over the inner sheath, whereby the curved axial bore can be formed of relatively straight and curved sections.

5. A method for providing access to a series of adjacent vertebrae located within a human lumbar and sacral spine having an anterior aspect, a posterior aspect and an axial aspect, wherein the axial aspect is curved in the posterior-anterior plane due to curvature of the spinal column, the vertebrae separated by intact or damaged spinal discs, the method comprising the steps of:

accessing an anterior or posterior sacral target point of a sacral vertebra in alignment with a visualized, curved axial instrumentation/fusion line extending in said axial aspect through the series of adjacent vertebral bodies; and from the accessed sacral target point, boring a plurality of trans-sacral axial bores through the vertebral bodies of said series of adjacent vertebrae and any intervertebral spinal discs, the plurality of trans-sacral axial bores commencing in substantial axial alignment with said axial instrumentation/fusion line at the anterior or posterior sacral target point and extending in the cephalad direction axially through the vertebral bodies of said series of adjacent vertebrae and any intervertebral spinal discs, each trans-sacral axial bore diverging away from the axial instrumentation/fusion line and any other axial bore and terminating at spaced apart cephalad bore ends.

6. The method of claim 5, wherein the boring step further comprises the steps of:

providing a boring, assembly comprising a boring head capable of being imaged at the distal end of a flexible boring drive shaft of materials that are and a directional control mechanism for adjusting a boring angle of the boring head; and in boring each of the plurality of trans-sacral axial bores:
imaging the boring head and the vertebrae;
while observing the imaged boring head and vertebrae, advancing the boring head from the anterior or posterior target point initially in alignment with the axial instrumentation/fusion line and then in the cephalad direction through the vertebral bodies and any intervening discs; and
during advancement, adjusting the boring angle of the boring head to bore the axial bore diverging away from the axial instrumentation/fusion line and any other axial bore of the plurality of diverging axial bores.

7. The method of claim 6, wherein the adjusting step further comprises the steps of:

straightening the boring angle of the boring head when boring through opposed end faces of facing vertebral bodies and the intervening disc space so that the axial bore is aligned axially normal to the opposed end faces of the facing vertebral bodies; and deflecting the boring angle of the boring head when boring within a vertebral body between the end faces of the vertebral body, whereby the curved axial bore can be formed of relatively straight and curved sections.

8. The method of claim 5, wherein the boring step further comprises the steps of:

providing a boring assembly comprising a boring drill bit capable of being imaged at the distal end of a flexible drive shaft, the drive shaft coupled at a drive shaft proximal end to a drill motor and at a drive shaft distal end to the drill bit, whereby the drill bit and drive shaft are rotatable by operation of the drill motor, a flexible inner sheath having an inner sheath lumen through which said drive shaft extends said inner sheath having a curved distal segment, and a straight flexible outer sheath having an outer sheath lumen through which said inner sheath extends, the outer and inner sheaths providing directional control to the boring angle of the drill bit by selectively distally advancing or proximally retracting the outer sheath over or from a distal segment of the inner sheath; and operating the drill motor and advancing the drill bit from the anterior or posterior target point while adjusting the boring angle of the drill bit by selectively advancing or retracting the outer sheath over or from the distal segment of the inner sheath to drill the diverging axial bore through the vertebral bodies and any intervening discs.

9. The method of claim 8, wherein the adjusting step further comprises the steps of:

straightening the boring angle of the drill bit when boring through opposed end faces of facing vertebral bodies and the intervening disc space by extending the outer sheath distally over the inner sheath so that the axial bore is aligned axially normal to the opposed end faces of the facing vertebral bodies by advancing the outer sheath distally over the drive shaft; and deflecting the boring angle of the drill bit when boring within a vertebral body between the end faces of the vertebral body by retracting the outer sheath proximally over the inner sheath, whereby the curved axial bore can be formed of relatively straight and curved sections.

10. The method of claim 5, wherein the boring step further comprises the steps of:

providing a boring assembly comprising a boring drill bit capable of being imaged at the distal end of a flexible drive shaft, the drive shaft coupled at a drive shaft proximal end to a drill motor and at a drive shaft distal end to the drill bit, whereby the drill bit and drive shaft are rotatable by operation of the drill motor, a drive shaft sheath extending between a drive shaft sheath proximal end to a drive shaft sheath distal end and having a drive shaft sheath lumen through which said drive shaft extends, a tip deflection wire extending from a tip deflection wire distal end coupled with the drive shaft distal end to a tip deflection wire proximal end, the tip deflection wire providing directional control to the boring angle of the drill bit by selectively applying tension to or releasing tension from the tip deflection wire proximal end while advancing the drill bit to bore a curved axial bore visualized by observation of the imaged drill bit and vertebrae of the spine; and operating the drill motor and advancing the drill bit and drive shaft from the anterior or posterior target point while adjusting the boring angle of the drill bit by selectively applying tension to or releasing tension from the tip deflection wire from the tip deflection wire proximal end to drill the diverging axial bore through the vertebral bodies and any intervening discs.

11. The method of claim 10, wherein the adjusting step further comprises the steps of:

releasing tension from the tip deflection wire to straighten the boring angle of the drill bit when boring through opposed end faces of facing vertebral bodies and the intervening disc space so that the axial bore is aligned axially normal to the opposed end faces of the facing vertebral bodies; and applying tension to the tip deflection wire to deflect the boring angle of the drill bit when boring within a vertebral body between the end faces of the vertebral body, whereby the curved axial bore can be formed of relatively straight and curved sections.

12. The method of claim 5, wherein the boring step further comprises the steps of:

providing a boring assembly comprising a boring drill bit capable of being imaged at the distal end of a flexible drive shaft, the drive shaft coupled at a drive shaft proximal end to a drill motor and at a drive shaft distal end to the drill bit, whereby the drill bit and drive shaft are rotatable by operation of the drill motor, a flexible drive shaft sheath enclosing and extending along the drive shaft to a drive shaft sheath distal end, the drive shaft sheath having a sheath axis and a sheath lumen extending between the drive shaft sheath proximal and distal ends through which the drive shaft extends, the sheath lumen disposed off center from the sheath axis, whereby the drive shaft sheath provides directional control to the boring angle of the drill bit by selectively advancing the drive shaft sheath over a distal segment of the drive shaft to apply the drive shaft sheath distal end against a surface of the drill bit to urge the drill bit in the direction that the off center sheath lumen is from the sheath axis thereby imparting an offset boring angle to the drill bit or by retracting the drive shaft sheath from the distal segment of the drive shaft to enable the drive shaft section extended distally from the drive shaft sheath to straighten; and operating the drill motor and advancing the drill bit and drive shaft and drive shaft sheath from the anterior or posterior target point while adjusting the boring angle of the drill bit by selectively advancing the drive shaft sheath or retracting the drive shaft sheath over or from the distal segment of the drive shaft to drill the diverging axial bore through the vertebral bodies and any intervening discs.

13. The method of claim 12, wherein the adjusting step further comprises the steps of:

retracting the drive shaft sheath proximally over the drive shaft to straighten the boring angle of the drill bit when boring through opposed end faces of facing vertebral bodies and the intervening disc space so that the axial bore is aligned axially normal to the opposed end faces of the facing vertebral bodies by; and advancing the drive shaft sheath distally over the drive shaft to deflect the boring angle of the drill bit when boring within a vertebral body between the end faces of the vertebral body, whereby the curved axial bore can be formed of relatively straight and curved sections.

14. A method for providing access to a series of adjacent vertebrae located within a human lumbar and sacral spine having an anterior aspect, a posterior aspect and an axial aspect, wherein the axial aspect is curved in the posterior-anterior plane due to curvature of the spinal column, the vertebrae separated by intact or damaged spinal discs, the method comprising the steps of:

accessing an anterior or posterior sacral target point of a sacral vertebra in alignment with a visualized, curved axial instrumentation/fusion line extending in said axial aspect through the series of adjacent vertebral bodies; and from the accessed sacral target point, boring a plurality of trans-sacral axial bores through the vertebral bodies of said series of adjacent vertebrae and any intervening spinal discs, the plurality of trans-sacral axial bores commencing in substantial axial alignment with said axial instrumentation/fusion line at the anterior or posterior sacral target point and extending in the cephalad direction axially through the vertebral bodies of said series of adjacent vertebrae and any intervertebral spinal discs, each trans-sacral axial bore diverging away from the axial instrumentation/fusion line and any other axial bore and terminating at spaced apart cepahalad bore ends;

wherein the boring step further comprises the steps of:

providing a boring assembly comprising a boring head capable of being imaged at the distal end of a flexible boring drive shaft and a directional control mechanism for adjusting a boring angle of the boring head;

imaging the boring head and the vertebrae;

while observing the imaged boring head and vertebrae, advancing the boring head from the anterior or posterior target point through the vertebral bodies and any intervening discs; and during advancement, adjusting the boring angle of the boring head to form one or more curves in any of the plurality of diverging axial bores.

15. The method of claim 14, wherein the adjusting step further comprises the steps of:

straightening the boring angle of the boring head when boring through opposed end faces of facing vertebral bodies and the intervening disc space so that the axial bore is aligned axially normal to the opposed end faces of the facing vertebral bodies; and deflecting the boring angle of the boring head when boring within a vertebral body between the end faces of the vertebral body, whereby one or more of the axial bores can be formed of relatively straight and curved sections.

* * * * *